United States Patent
Le Bihan

(10) Patent No.: US 10,942,239 B2
(45) Date of Patent: Mar. 9, 2021

(54) MRI METHOD FOR DETERMINING SIGNATURE INDICES OF AN OBSERVED TISSUE FROM SIGNAL PATTERNS OBTAINED BY MOTION-PROBING PULSED GRADIENT MRI

(71) Applicant: COMMISSARIAT A L'ENERGIE ATOMIQUE ET AUX ENERGIES ALTERNATIVES, Paris (FR)

(72) Inventor: Denis Le Bihan, Saint Nom la Breteche (FR)

(73) Assignee: COMMISSARIAT A L'ENERGIE ATOMIQUE ET AUX ENERGIES ALTERNATIVES, Paris (FR)

(*) Notice: Subject to any disclaimer, the term of this patent is extended or adjusted under 35 U.S.C. 154(b) by 352 days.

(21) Appl. No.: 15/555,958

(22) PCT Filed: Apr. 12, 2016

(86) PCT No.: PCT/EP2016/058040
§ 371 (c)(1),
(2) Date: Sep. 5, 2017

(87) PCT Pub. No.: WO2016/166115
PCT Pub. Date: Oct. 20, 2016

(65) Prior Publication Data
US 2018/0045802 A1  Feb. 15, 2018

(30) Foreign Application Priority Data
Apr. 13, 2015  (EP) .................................. 15305546

(51) Int. Cl.
*G01R 33/563* (2006.01)
*G01R 33/36* (2006.01)
(Continued)

(52) U.S. Cl.
CPC ........ *G01R 33/56341* (2013.01); *A61B 5/055* (2013.01); *A61B 5/489* (2013.01);
(Continued)

(58) Field of Classification Search
CPC .... A61B 5/055; A61B 5/489; G01R 33/3607; G01R 33/56341; G01R 33/5635; G01R 33/56358
See application file for complete search history.

(56) References Cited

U.S. PATENT DOCUMENTS 5,825,186 A  10/1998  Ehman et al.
5,899,858 A  5/1999  Muthupillai et al.
(Continued)

FOREIGN PATENT DOCUMENTS

JP  5-31099 A  2/1993
JP  8-206097 A  8/1996
(Continued)

OTHER PUBLICATIONS

S. Chabert et al., "Relevance of the information about the diffusion distribution in vivo given by Kurtosis in q-space imaging," Proceedings of the 12th Annual Meeting of Intl. Soc. Mag. Reson. Med. vol. 11, 2004, pp. 1238.

(Continued)

*Primary Examiner* — Joanne M Hoffman
*Assistant Examiner* — Alexei Bykhovski
(74) *Attorney, Agent, or Firm* — BakerHostetler

(57) ABSTRACT

A method for determining a signature index of an observed tissue comprises the step of providing a generic attenuation model of a motion-probing gradient pulse MRI attenuated signal S(b), and providing a reference model parameter vector ($p_R(i)$) corresponding to a reference state of the tissue. On the basis of the evolution of the determined partial differential sensitivities $dS_i(b)$ of the model attenuated signal (Continued)

S(b) to each model parameter p(i) at the neutral state attenuated signal $S_N(b)$ versus b values, a discrete and narrow size set of key b is built and a series of MRI images of the observed tissue are acquired by using the key b values. Then, for each voxel a signature index (sADC(V), Sdist(V), SCdist(V), Snl(V), SI(V)) of the voxel V is determined as a scalar function depending on a distance between the voxel signal pattern acquired at the key b values and the signal pattern of the reference state of the tissue at the same key b values. An apparatus is configured for implementing such a method.

22 Claims, 19 Drawing Sheets

(51) Int. Cl.
    *A61B 5/055*       (2006.01)
    *A61B 5/00*        (2006.01)
(52) U.S. Cl.
    CPC ..... *G01R 33/3607* (2013.01); *G01R 33/5635* (2013.01); *G01R 33/56358* (2013.01)

(56) References Cited

U.S. PATENT DOCUMENTS

| | | |
|---|---|---|
| 2005/0007100 A1 | 1/2005 | Basser et al. |
| 2012/0280686 A1 | 11/2012 | White et al. |
| 2014/0309520 A1 | 10/2014 | Lee |

FOREIGN PATENT DOCUMENTS

| | | |
|---|---|---|
| JP | 2005-519685 A | 7/2005 |
| JP | 2009-512528 A | 3/2009 |
| JP | 2014-204802 A | 10/2014 |
| WO | 2015/042416 A1 | 3/2015 |

OTHER PUBLICATIONS

R. N. Alkalay et al., "MR Diffusion is Sensitive to Mechanical Loading in Human Intervetebral Disk Ex Vivo," Journal of Magnetic Resonance Imaging, vol. 41, No. 3, Jun. 3, 2014, pp. 654-664, XP055207979.
H.A. Dyvorne et al., "Prospective Comparison of IVIM DWI, MR Elastography and Transient Elastography for the detection of liver fibrosis in HCV: Initial results," Proceedings of the International Society for Magnetic Resonance in Medicine, vol. 21, Apr. 6, 2013, pp. 4082, XP040631678.
Z. Yin et al., "Simultaneous MR Elastography and Diffusion Acquisitions: Diffusion-MRE (dMRE)," Magnetic Resonance in Medicine vol. 71, Mar. 19, 2014, pp. 1682-1688, XP055240526.
S. Ichikawa et al., "MRI-based staging of hepatic fibrosis: Comparison of intravoxel incoherent motion diffusion-weighted imaging with magnetic resonance elastography," Journal of Magnetic Resonance Imaging, vol. 42, No. 1, Sep. 15, 2014, pp. 204-210, XP055240425.
J. Choi et al., "Robust optimal design of diffusion-weighted magnetic resonance experiments for skin microcirculation," Journal of Magnetic Resonance, vol. 206, No. 2, Jul. 24, 2010, pp. 246-254, XP027276343.
U. Rudrapatna et al., "Can diffusion kurtosis imaging improve the sensitivity and specificity of detecting microstructural alterations in brain tissue chronically after experimental stroke? Comparisons with diffusion tensor imaging and histology," Neuroimage, vol. 97, Apr. 15, 2014, pp. 363-373, XP028873481.
S. Chawla et al., "Diffusion-weighted imaging in head and neck cancers," Future Oncology, 2009, vol. 5, pp. 959-975.
J. Jensen et al., "MRI quantification of non-Gaussian water diffusion by kurtosis analysis," NMR Biomedicine, 2010, vol. 23, pp. 698-710.
M. Iima et al., "Characterization of Glioma Microcirculation and Tissue Features Using intravoxel Incoherent Motion Magnetic Resonance Imaging in a Rat Brain Model," Investigative Radiology, 2014, vol. 49, No. 7, pp. 485-490.
M. Iima et al., "Quantitative Non-Gaussian Diffusion and Intravoxel Incoherent Motion Magnetic Resonance Imaging: Differentiation of Malignant and Benign Breast Lesions," Investigative Radiology, vol. 50, No. 4, Apr. 2015, pp. 205-211.
Jensen et al., "Diffusional kurtosis imaging: the quantification of non-gaussian water diffusion by means of magnetic resonance imaging," Magnetic Resonance in Medecine, 2005; vol. 53, No. 6, pp. 1432-1440.
R. Mulkern et al., "On high b diffusion imaging in human brain: ruminations and experimental insights," Magnetic Resonance Imaging, 2009, No. 27, No. 8, pp. 1151-1162.
D. Yablonskiy et al., "Statistical model for diffusion attenuated MR signal," Magnetic Resonance in Medicine, 2003, vol. 50, No. 4, pp. 664-669.
K. Bennett et al., "Characterization of continuously distributed cortical water diffusion rates with a stretched exponential model," Magnetic Resonance in Medicine, 2003, vol. 50, No. 4, pp. 727-734.
M. Hall et al., "From diffusion-weighted MRI to anomalous diffusion imaging," Magnetic Resonance in Medicine, 2008, vol. 59, No. 3, pp. 447-455.
Thou et al., "Studies of anomalous diffusion in the human brain using fractional order calculus," Magnetic resonance in Medicine, 2010, vol. 63, No. 3, pp. 562-569.
K. Glaser et al., "Shear Stiffness Estimation Using Intravoxel Phase Dispersion in Magnetic Resonance Elastography," Magnetic Resonance in Medicine, 2003, vol. 50, pp. 1256-1265.
Poot et al., "Optimal Experimental Design for Diffusion Kurtosis Imaging," IEEE Transactions on Medical Imaging, vol. 29, No. 3, Mar. 3, 2010, pp. 819-829, XP011304045.
N. White et al., "Optimal diffusion MRI acquisition for fiber orientation Density Estimation: An analytic approach," Human Brain Mapping, vol. 30, No. 11, Jul. 14, 2009, pp. 3696-3703, XP055208313.
Z. Qinwei et al., "Cramér-Rao bound for intravoxel incoherent motion diffusion weighted imaging fitting," The Effect of Applied Compressive Loading on Tissue-Engineered Cartilage Constructs Cultured with TGF-BETA3, Jul. 3, 2013, pp. 511-514, XP032489172.
Fabrizio Fasano et al., "A highly sensitive radial diffusion measurement method for white matter tract investigation," Magnetic Resonance Imaging, vol. 27, 2009, pp. 519-530.
Koay et al., "Sparse and optimal acquisition design for diffusion MRI and beyond," Medical Physics, vol. 39, No. 5, Apr. 16, 2012, pp. 2499-2511, XP012161006.
English Translation of Notice of Rejection issued in Japanese Patent Application No. 2017-552809 dated Aug. 18, 2020.

MRI METHOD FOR DETERMINING SIGNATURE INDICES OF AN OBSERVED TISSUE FROM SIGNAL PATTERNS OBTAINED BY MOTION-PROBING PULSED GRADIENT MRI

CROSS-REFERENCE TO RELATED APPLICATIONS

This application is a National Stage of International patent application PCT/EP2016/058040, filed on Apr. 12, 2016, which claims priority to foreign European patent application No. EP 15305546.2, filed on Apr. 13, 2015, the disclosures of which are incorporated by reference in their entirety.

FIELD OF THE INVENTION

The invention relates to the field of the use of magnetic resonance imaging in medicine. The invention concerns a method to determine one or several signature indices of tissues from signal patterns obtained by motion-probing pulsed gradient (MPG) Magnetic Resonance Imaging (MRI).

BACKGROUND

Diffusion MRI, also designated dMRI is one such MPG MRI method which has been widely used for the diagnosis and monitoring of various lesions, notably stroke and cancer, as described in the paper of Chawla S. and al., entitled "Diffusion-weighted imaging in head and neck cancers" and published in Future Oncology, 2009, Vol. 5, pages 959-975 (Ref.#1). The reason explaining such wide use is the fact that, during their diffusion-driven displacements, water molecules interact with many cellular or tissue components such as fibers or membranes, providing important clues on tissue microstructure.

As a result diffusion in tissues is not "free" and does not follow a Gaussian distribution.

Recently and as described in the paper from Jensen J. H. et al., entitled "MRI quantification of non-Gaussian water diffusion by kurtosis analysis", published in NMR in biomedicine, 2010, 23: 698-710 (Ref.#2), in a first paper from lima M. et al., entitled "Characterization of Glioma Microcirculation and Tissue Features Using intravoxel Incoherent Motion Magnetic Resonance Imaging in a Rat Brain Model, published in Investigative radiology, 2014, 49(7): 485-490 (Ref.#3), and in a second paper from lima M. et al., entitled "Quantitative Non-Gaussian Diffusion and Intravoxel Incoherent Motion Magnetic Resonance Imaging: Differentiation of Malignant and Benign Breast Lesions", published in Investigative radiology Sep. 25, 2014 (Ref.#4), it has been established that beyond the original Gaussian Apparent Diffusion Concept (ADC), non-Gaussian diffusion parameters (e.g. mean diffusion, $ADC_0$, and Kurtosis, K) provide further important information on tissue microstructure. Furthermore, MPG MRI is also sensitive to other kinds of so-called Intra Voxel Incoherent Motions (IVIM), such as microcirculation of blood in small tissue vessels (perfusion).

The current approaches to characterize a type of tissue or a biological feature owned by a type of tissue are mainly based on a direct estimation of model parameters that are assumed to be as one or several of them sensitive to a type of tissue and/or a biological property owned by the tissue. As an example, one parameter or a set of parameters that is below or above one threshold value or a set of threshold values may correspond to malignant or benign nature of a lesion.

However, the accurate estimation of such diffusion and IVIM related parameters requires fitting the MPG MRI signal with biophysical models using algorithms which are often prone to errors and calculation intensive, preventing real time analysis to be performed. Furthermore, accurate data fitting with models also requires acquisition of multiple images with a large range of MPG values for diffusion sensitization so called b values, resulting in long acquisition time.

The technical problem is to provide a method for determining directly a signature index, sensitive with a high contrast to a type of tissue and/or a biological property owned by the tissue to cut acquisition and processing times.

SUMMARY OF THE INVENTION

To that end, the invention relates to a method for determining one or several indices of an observed tissue, representative sensitively of a type of tissue or representative sensitively of a microstructure or biological state of a type of tissue, the signature indices being determined from motion-probing pulses gradient Magnetic Resonance Images (MRI) of the observed tissue, and the method comprising the steps of:
  providing in a first step a generic attenuation model of a diffusion MRI attenuated signal S(b), representative of the type of the tissue to be observed, suited to Intra Voxel Incoherent Motion (IVIM) and/or non-Gaussian signal patterns, and expressed by a model function f(b), depending on a gradient attenuation factor b and on a first set of model parameters p(i) characterizing when valued the type of tissue and the microstructure state, said model parameters p(i) defining a model parameter vector space and NP being the number model parameters of the first set; then
  providing in a second step a reference model parameter vector ($p_R(i)$) corresponding to a neutral or an average or a specific state of the tissue, defining through the generic attenuation model a neutral reference model diffusion MRI attenuated signal $S_R(b)$; then
  for each model parameter p(i), determining in a third step a key b value that maximizes a partial differential sensitivity $dS_i(b)$ of the generic model diffusion MRI attenuated signal S(b) to the said model parameter p(i) at the reference model parameter vector ($p_R(i)$) over a predetermined interval of b values ranging from zero to a predetermined maximum value $b_{max}$; then
  determining in the fourth step from the NP key b values determined in the third step a key b value subset by removing the key b values that are associated to model parameters of low interest for tissue type and/or the microstructure or biological state to characterize; then
  acquiring in a fifth step a set of MRI images of a Field Of View (FOV) of the observed tissue by means of a motion-probing pulsed Gradient MRI sequence programmed with gradient configured to obtain the determined subset of key b values; then
  on a one-per-one voxel basis or on a predetermined Region Of Interest (ROI) including a set of voxels, determining a signature index sADC(V), Sdist(V), SCdist (V), Snl(V), SI(V)) of the voxel V or the ROI as a real number representative of the microstructure state and the type of the tissue present in the ROI or the voxel V, the signature index being a scalar function depending on the voxel(s) signals acquired at the key b values of the key b value subset.

According to specific embodiments, the method for determining one or several indices, comprises one or more of the following features:

during the determining of the key b values subset, a further filtering is carried out by removing the key b values that provide the MRI signal with a sensitivity $dS_i(b)$ to the model parameters $p(i)$ around the reference signal $S_R(b)$ below a predetermined sensitivity threshold and/or that higher than the validity range of the used generic attenuation model and/or which may results in values below a predetermined noise threshold level;

the key b values subset has a cardinality equal to 2 and includes a low key b value Lb and a high key b value Hb, and the signature index of a voxel is a signature index of a first kind, designated by sADC and calculated according to the expression:

$$sADC(V) = Ln\ [S_V(Lb)/S_V(Hb)]/(Hb-Lb)$$

where $S_V(Lb)$ designates the measured signal of the voxel for the MRI image acquired with the key b=Lb, and $S_V(Hb)$ designates the measured signal of the voxel for the MRI image acquired with the key b=Hb;

the signature index is a signature index of a second kind, designated as Sdist, that is determined by calculating a pseudo-distance between the vector signal pattern observed at the key b values $b_k$ in the ROI or voxel $S_V(b_k)$ and the vector signal pattern calculated in the reference state tissue R using the generic attenuation model $S_R(b_k)$, k designating an integer rank of the key values running over the key b values subset; and the pseudo-distance is an algebraic distance or a correlation coefficient or a scalar product between $S_V(b_k)$ and $S_R(b_k)$ or any kind of distance;

the signature index of second kind Sdist is calculated by the expression:

$$Sdist(V) = \sum_{b_k \in key\ b\ values} (-1)^{G(b_k)} [S_V(b_k) - S_R(b_k)]/S_R(b_k)$$

where $G(b_k)$ is an integer that can be even or odd depending on the sign of $dS(b_k)$ with $dS(b_k)=[S_V(b_k)-S_R(b_k)]/S_R(b_k)$;

the signature index is an extension of a signature index of a second kind, designated by SCdist, that is determined by calculating a pseudo-distance between an 2D-array signal pattern $S_V(b_{k(m)},Cm)$ observed at different key $\underline{b}$ values $b_{k(m)}$ under different conditions Cm in the ROI or voxel and the 2-D-array signal pattern $S_R(b_{k(m)},Cm)$, calculated in a reference state tissue R using a generic attenuation model, where m designates an index identifying the MPG condition in a set of MPG conditions ranging from 1 to a integer number $\underline{c}$, and k(m) designates the integer rank of the key b values of the subset corresponding to the condition Cm, and the pseudo-distance is an algebraic distance or a correlation coefficient or a scalar product between $S_V(b_{k(m)}, Cm)$ and $S_R(b_{k(m)},Cm)$ or any kind of distance, a particular distance being defined as:

$$SCdist(V; R) = \sum_{m=1\ to\ c;\ b_k(m) \in key\ b\ values} (-1)^{G(b_k(m),Cm)} [S_V(b_k(m), Cm) - S_R(b_k(m), Cm)]/S_R(b_k(m), Cm)$$

where $G(b_{k(m)}),Cm)$ is an integer that can be even or odd depending on the sign of $[S_V(b_k(m),Cm)-S_R(b_k(m),Cm)]/S_R(b_k(m),Cm)$; and particular conditions Cm being different orientations in space of the MPG pulses to take into account diffusion anisotropy and/or different diffusion times, defined by the time interval and the duration of the MPG, to take into account restricted diffusion effects;

the here above method comprises the steps of:

calculating a number $\underline{r}$ of signature distances, $Sdist(V;R_j)$ or $SCdist(V;R_j)$, between the observed tissue and different predetermined reference tissues Rj, wherein j is an integer index identifying the reference tissue Rj and is ranging from 1 to $\underline{r}$, and wherein $Sdist(V;R_j)$ and $SCdist(V;R_j)$ are respectively defined here above; then identifying the tissue state or type of the observed tissue as that of the reference tissue $R_{j0}$, where the reference tissue index $j_0$ is such that:

$$Sdis(V;Rj_0)=Min_{j=1\ to\ r}(Sdist(V;R_j))$$

or $$SCdis(V;Rj_0)=Min_{j=1\ to\ r}(SCdist(V;R_j));$$

the method comprises further between the first step and the second step, a seventh step of providing a first pole reference model parameter vector $(p_{P1}(i))$ and a second pole reference parameter vector $(p_{P2}(i))$, corresponding each one to a first calibrating state P1 and a second calibrating state P2 of the same type of tissue as the observed tissue, and calculated from preliminary MRI images acquired in a preliminary step of calibration, or from previously established values, the first and second calibrating states P1, P2, as well their corresponding reference model parameter vectors $(p_{P1}(i)),(p_{P2}(i))$, being significantly different;

the second step is replaced by an eight step of:

calculating a neutral reference model parameter vector $p_N(i)$ as the average sum of the first pole reference model parameter vector $(p_{P1}(i))$ and the second pole reference parameter vector $(p_{P2}(i))$;

the first calibrating state P1 of the tissue to the second calibrating state P2 correspond to a "benign" versus "malign" tissue for a tumor tissue, or a tissue under medical treatment versus an untreated tissue, or a "resting" versus an "activated" tissue, or a "normal" versus an "inflammatory" tissue, or a tissue with a "first spatial orientation" versus a tissue with a "second spatial orientation" for an anisotropic tissue as in muscles, the heart or brain white matter tissue, or a tissue with a "first kind of cytoarchitectony" versus a tissue with "a second kind of architectony" for a brain cortex tissue;

the signature index is a normalized signature index of a third kind, designated as Snl, that uses a signature index of a second kind Sdist and is determined by using the expression:

$$Snl(V) = \{max([Sdist(V)/Sdist1],0) - [max([Sdist(V)/Sdist2],0)\}$$

where Sdist(V) is the second kind signature index of the voxel of the tissue under investigation, Sdist1 is the second kind signature index of the voxel of the first calibrating state
P1, and Sdist2 is the second kind signature index of the
voxel of the second calibrating state P2;

the signature index is an absolute signature SI determined
by scaling the normalized signature index Snl with a
strictly monotonous function;

ROI level statistics on absolute signature SI are determined such as mean, standard deviation, skewness or kurtosis for lesion heterogeneity, or malignant charge volume defined as the product of the voxel size and the number of voxels with a SI index above a predetermined malignant threshold, and/or histograms are determined; and/or Images of absolute signature index SI are displayed using a color scale and shown with Im 3D rendering;

the type of tissue is a tissue of the organs consisting of the brain, head and neck organs, breast, prostate, liver, pancreas, lung, heart, muscle or joints; and/or the generic attenuation model is comprised in the set of model consisting of the polynomial or Kurtosis model, the bi-exponential model, the statistical model and the stretched model;

the generic attenuation model is the IVIM/Kurtosis model and its model function S(b) is expressed as:

$$S(b)=[S_0^2\{f_{IVIM}\exp(-b\cdot D^*)+(1-f_{IVIM})\exp[-b\cdot ADC_0+(b\cdot ADC_0)^2 K/6]\}^2+NCF]^{1/2}$$

where $S_0$ is the signal acquired with no diffusion weighting for b equal to zero, $f_{IVIM}$ is the volume fraction of incoherently flowing blood in the tissue, D* is the pseudo-diffusion coefficient associated to the IVIM effect, $ADC_0$ is the virtual Apparent Diffusion Coefficient which would be obtained when b approaches 0, K is the kurtosis parameter K, and NCF is the Noise Correction Factor;

the subset of key b values has a cardinality equal to 2 and includes a low key b value Lb and a higher key b value Hb, and a normalized signature index Snl of a voxel, designated by Snl(V) is calculated according to the expression:

$$Snl(V) = \begin{Bmatrix} \max([dS_V(Hb) - dS_V(Lb)]/[dS_{P1}(Hb) - dS_{P1}(Lb)], 0) \\ -[\max([dS_V(Hb) - dS_V(Lb)]/[dS_{P2}(Hb) - dS_{P2}(Lb)], 0) \end{Bmatrix}$$

with $dS_X(b)=[S_X(b)-S_N(b)]/S_N(b)$ for X=V, P1, P2 and for b=Hb, Lb; $S_{P1}(b)$, $S_{P2}(b)$, $S_N(b)$ being the signals corresponding respectively to a first actual state P1, a second actual state P2, and a neutral state previously identified by the model and their respective first pole reference model parameter vector ($p_{ref(Q1)}(i)$), second pole reference parameter vector ($p_{ref(Q2)}(i)$), and neutral reference model parameter vector ($p_N(i)$) so that the signals values $S_{P1}(Lb)$, $S_{P2}(Lb)$, $S_N(Lb)$, $S_{P1}(Hb)$, $S_{P2}(Hb)$, $S_N(Hb)$ can be calculated, and where $S_V(Lb)$ designates the measured signal of the voxel for the MRI image acquired with the lower key b value Lb, and $S_V(Hb)$ designates the measured signal of the voxel for the MRI image acquired with the higher key b value Hb;

the method comprises further a step of displaying at least one map of at least one signature index of the voxels belonging to the Region Of Interest.

The invention also relates to an IVIM angiography method for recognizing blood vessels from an observed tissue comprising the steps of:

determining one or several maps of at least one signature index of the voxels of the observed tissue by using a method as defined here above that determines a sADC or Snl index and an IVIM/non-Gaussian model generic attenuation signal model, wherein either a first low key b value Lb equal to zero and a high key b value Hb for which the signal decay due to the IVIM effect in a voxel containing only blood is above a predetermined threshold are selected, and a signature index sADC is determined, or a voxel containing a large blood vessel is considered as a first pole reference tissue and a voxel without a large blood vessel is considered as a second pole reference tissue, and a normalized signature index Snl is determined as defined here above; and deriving and displaying angiograms from the at least one signature index maps.

The invention also relates to an IVIM Magnetic Resonance Elastography method for determining real IVIM elastograms and/or a contrasted shear stiffness of an observed tissue comprising the steps of:

selecting two key b values in view of a generic IVIM/elastography attenuation model, and providing a first pole parameter vector and a second pole parameter vector that correspond respectively to a calibrated high shear stiffness and a calibrated low shear stiffness, the first pole reference model parameter vector ($p_{P1}(i)$), second pole reference parameter vector ($p_{QP2}(i)$) being previously identified once for all during a preliminary calibration process carried with induced shear waves at a predetermined shear waves frequency a predetermined frequency f comprised in an interval ranging from 25 Hz to 500 Hz; then applying mechanical vibrations at the predetermined frequency $\underline{f}$ to induce shear waves in the observed tissue while acquiring a set of Magnetic Resonant Elastography images of a Field of View (FOV) of the tissue by using the two selected key b values; then determining on a one-per-one voxel basis or on a predetermined Region Of Interest (ROI) including a set of voxels, an elasticity signature index eSnl or eSI by using a same kind of calculation as for the signature index Snl or SI defined here above.

According to specific embodiments, the method IVIM Magnetic Resonance Elastography method for determining real IVIM elastograms and/or a contrasted shear stiffness of an observed tissue comprises one or more of the following features:

two sets of MRE images are acquired with phase offsets θ separated by π/2 and averaged before calculating the elasticity index eSI.

The invention also relates to a virtual IVIM Magnetic Resonance Elastography method for emulating virtual IVIM MR elastograms of an observed tissue comprising a step of simulating and displaying virtual elastograms of the observed tissue, either by using a generic IVIM/elastography attenuation model wherein the MRE attenuated signal $S/S_0$ depends on the shear stiffness and the frequency and by replacing in the generic model the mapped shear stiffness by a normalized elasticity signature index eSI as determined here above, or by using the same generic IVIM/elastography attenuation model and by calculating the mapped shear stiffness of the tissue from a normalized a mapped IVIM/diffusion signature index Snl as determined in the claim trough the relationship:

$$\mu=g(Snl)$$

where g(·) is a predetermined transformation function.

The invention also relates to an apparatus for determining a signature index of an observed tissue, representative sensitively of a type of tissue or representative sensitively of a microstructure or biological state of a type of tissue, the signature indices being determined from motion-probing pulses gradient Magnetic Resonance Images (MRI) of the observed tissue, comprising:
- a magnetic resonance imaging scanner to operate motion-probing pulses gradient Magnetic Resonance Imaging with a high resolution and accuracy and a means for controlling the scanner and processing the imaging data acquired by the scanner;
- the magnetic resonance imaging scanner being configured for acquiring a set of MRI images of a Field Of View (FOV) of the observed biological issue by using a same motion-probing pulses gradient sequence programmed with gradient configured to obtain determined subset of key b values; and
- the means for controlling the scanner and processing the imaging data acquired by the scanner comprising:
  - a means for storing a generic attenuation model of a diffusion MRI attenuated signal S(b), representative of the type of the tissue to be observed, suited to Intra Voxel Incoherent Motion (IVIM) and/or non-Gaussian signal patterns, and expressed by a model function f(b), depending on a gradient attenuation factor b and on a first set of NP model parameters p(i) characterizing the type of tissue and the microstructure state, said model parameters p(i) defining a model parameter vector space; and a reference model parameter vector ($p_R(i)$) corresponding to a neutral or an average or a specific state of the tissue, defining through the generic attenuation model a neutral reference model diffusion MRI attenuated signal $S_R(b)$; and/or a first pole reference model parameter vector ($p_{P1}(i)$) and a second pole reference parameter vector ($p_{P2}(i)$), corresponding each one to a first calibrating state P1 and a second calibrating state P2 of the same type of tissue as the observed tissue, and calculated from preliminary MRI images acquired in a preliminary step of calibration, or from previously established values, the first and second calibrating states P1, P2, as well their corresponding reference model parameter vectors ($p_{P1}(i)$),($p_{P2}(i)$), being significantly different;
  - a processing means configured for,
    - for each model parameter p(i), determining a key b value that maximizes a partial differential sensitivity $dS_i(b)$ of the generic model diffusion MRI attenuated signal S(b) to the said model parameter p(i) at the reference model parameter vector ($p_R(i)$) over a predetermined interval of b values ranging from zero to a predetermined maximum value $b_{max}$; and
    - determining from the NP key b values a key b value subset by removing the key b values that are associated to model parameters of low interest for tissue type and/or the microstructure or biological state to characterize; and/or calculating a neutral reference model parameter vector $p_N(i)$ as the average sum of the first pole reference model parameter vector ($p_{P1}(i)$) and the second pole reference parameter vector ($p_{P2}(i)$), when such pole reference model parameter vectors are provided; and
    - on a one-per-one voxel basis or on a predetermined Region Of Interest (ROI) including a set of voxels, determining a signature index (sADC(V), Sdist(V), Snl(V), SI(V)) of the voxel V as a real number representative of the microstructure state and the type of the tissue present in the ROI or the voxel V, the signature index being a scalar function depending on the voxel(s) signals acquired at the key b values of the key b value subset.

The invention also relates to a computer software comprising a set of instructions stored in the apparatus as defined here above and configured to carry out the steps of the method as defined here above when they are executed by the apparatus.

BRIEF DESCRIPTION OF THE DRAWINGS

The invention will be better understood from a reading of the description of several embodiments below, given purely by way of example and with reference to the drawings, in which:

FIG. 17 is a flow chart of a variant of the IVIM elastography method of;

DETAILED DESCRIPTION

Figure 1:
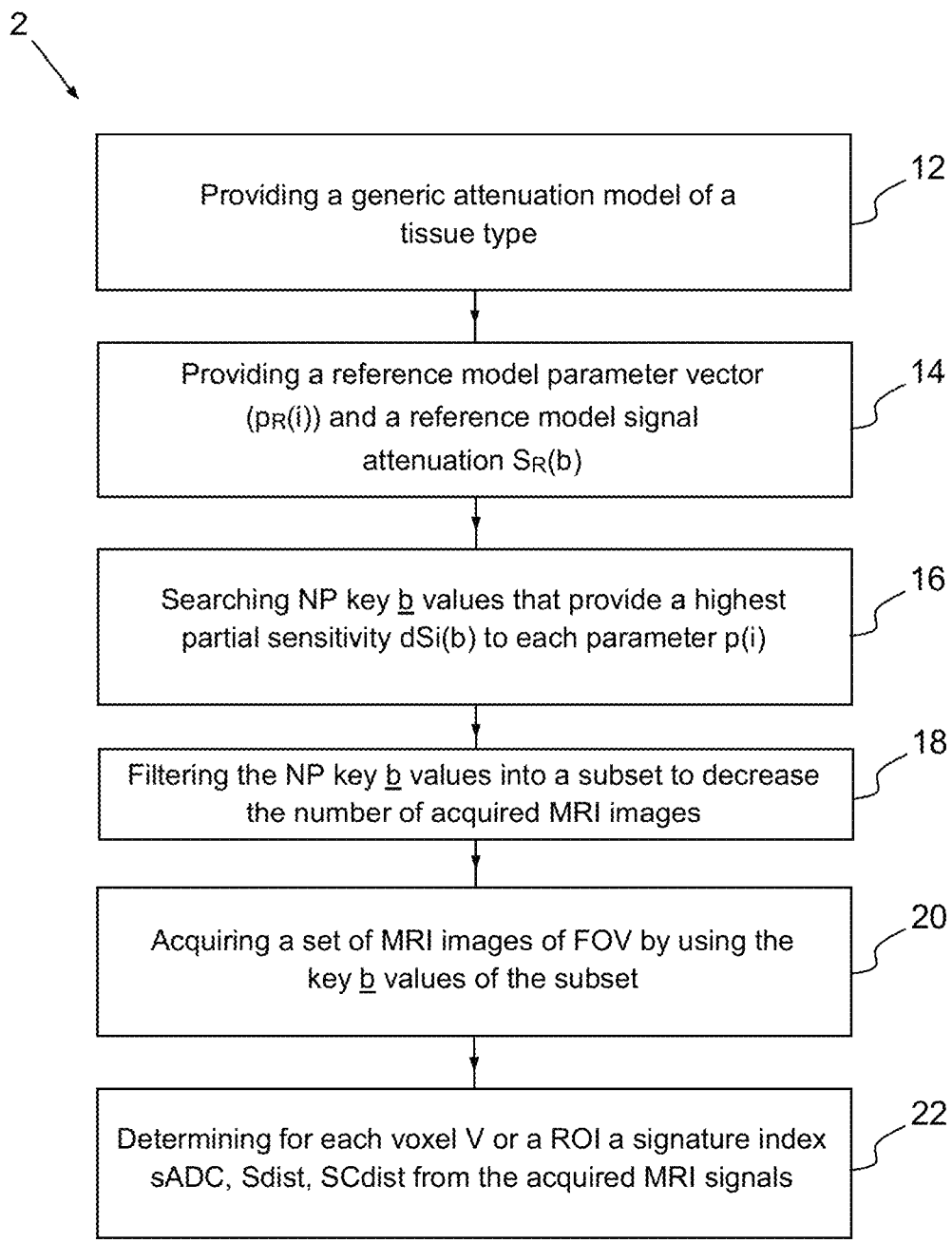
FIG. 1 is a general flow chart of a MRI method according to the invention for determining one or several signature indices of an observed tissue from motion-probing pulses gradient Magnetic Resonance Images (MRI)

As shown in FIG. 1 and according to the invention, a method 2 for determining one or several signature indices of an observed tissue, representative sensitively of a type of tissue or representative sensitively of a microstructure or a biological state of a type of tissue from motion-probing pulses gradient Magnetic Resonance Images (MRI) of the observed tissue, comprises a set of steps 12, 14, 16, 18, 20, 22.

In a first step 12, a generic signal attenuation model of a MPG MRI attenuated signal S(b) in terms of amplitude or modulus is provided. This generic attenuation model is representative of the signal pattern observed in a tissue in the presence of Intra Voxel Incoherent Motion (IVIM) and/or non-Gaussian diffusion effects, but does not necessarily implies a direct physical relationship with tissue structure. The generic attenuation model is expressed by a model function f(b) depending on a gradient attenuation factor b, so called "b value", and on a first set of model parameters p(i) characterizing when valued the microstructure state of the tissue, the said model parameters p(i) defining a model parameter vector space, i.e. a state vector space. The dimension of the model parameter vector space is equal to the number NP of parameters used in the generic attenuation model, and $\underline{i}$ is an integer, identifying a coordinate rank in the model parameter vector space and ranging from 1 to NP.

The generic attenuation model may be as examples the polynomial or Kurtosis model also called Diffusion Kurtosis Imaging, the bi-exponential model, the statistical model, the stretched exponential model, a fifth other model (not named), and a sixth other model (not named).

As a first model, the polynomial or Kurtosis model also called Diffusion Kurtosis Imaging is described in the article of Chabert et al., entitled "Relevance of the information about the diffusion distribution in vivo given by Kurtosis in q-space imaging", published in Proceedings of the 12$^{th}$ Annual Meeting of ISMRM Kyoto, Japan (Ref.#5), or in the article of Jensen J. H. et al., entitled "Diffusional kurtosis imaging: the quantification of non-gaussian water diffusion by means of magnetic resonance imaging, published in Magnetic Resonance in Medecine, 2005; 53(6):1432-1440 (Ref.#6).

As a second model, the bi-exponential model is described in the article of Mulkern R. V. et al., entitled "On high $\underline{b}$ diffusion imaging in human brain: ruminations and experimental insights", published in Magnetic Resonance Imaging, 2009; 27(8): 1151-1162 (Ref.#7).

As a third model, the statistical model is described in the article of Yablonskiy D. A. et al., entitled "Statistical model for diffusion attenuated MR signal", published in Magnetic Resonance in Medicine; 2003; 50(4):664-669 (Ref.#8).

As a fourth model, the stretched exponential model is described in the article of Bennett K. M., entitled "Characterization of continuously distributed cortical water diffusion rates with a stretched exponential model", published in Magnetic Resonance in Medicine; 2003; 50(4): 727-734 (Ref.#9).

The fifth model is described in the article of Hall M. G. et al., entitled "From diffusion-weighted MRI to anomalous diffusion imaging", published in Magnetic Resonance in Medicine; 2008; 59(3):447-455 (Ref.#10).

The sixth model is described in the article of Zhou X. J. et al., entitled "Studies of anomalous diffusion in the human brain using fractional order calculus", published in Magnetic resonance in Medicine; 2010; 63(3):562-569 (Ref.#11).

As examples, when using the IVIM/Kurtosis model described in the second article of lima M. et al (Ref.#4), the model parameters p(i) are comprised in the family consisting of the volume fraction $f_{IVIM}$ of incoherently flowing blood in the tissue, the pseudo-diffusion coefficient D* associated to the IVIM effect, the virtual Apparent Diffusion Coefficient $ADC_0$ which would be obtained when $\underline{b}$ approaches 0, the kurtosis parameter K.

In a second step 14, a reference model parameter vector ($p_R(i)$) is provided. The reference model parameter vector ($p_R(i)$) corresponds to a neutral or an average state of the tissue/organ under interest, or to the contrary to a specific state of tissue (for instance malignant) or to a targeted tissue type, as for instant a blood vessel, and defines through the generic attenuation model a reference MPG MRI attenuated signal $S_R(b)$.

The reference model parameter vector ($p_R(i)$) corresponds generally to a reference state of the tissue.

Then, in a third step 16, NP key b values are searched to provide the highest sensitivity of the motion-probing gradient MRI signal for each model parameter p(i) of coordinate rank $\underline{i}$, the values of the parameters varying around the reference model parameter vector ($p_R(i)$). To do so, one determines the evolution of a partial differential sensitivity $dS_i(b)$ of the model diffusion MRI attenuated signal S(b) to the said model parameter p(i) at the reference model diffusion MRI attenuated signal $S_R(b)$ versus the b values ranging from zero to a predetermined maximum value $b_{max}$ depending of the technical performance of the MRI scanner.

As an example, the partial differential sensitivity $dS_i$ at a given $\underline{b}$ value defined by the expression:

$$dS_i(b) = [S_{(1+\alpha)*p_R(i)}(b) - S_R(b)]/S_R(b) \qquad \text{Equation \#1}$$

where α designates a fixed increase of p(i) expressed in percentage for instance 10%, $S_{(1+\alpha)*p_R(i)}(b)$ is defined by the expression:

$$S_{(1+\alpha)*p_R(i)}(b) = S(b; p_R(1), \ldots, p_R(i-1), (1+\alpha)* p_R(i), p_R(i+1), \ldots, p_R(NP)) \qquad \text{Equation \#2}$$

Other expressions may be used that reflects such a concept of partial differential sensitivity $dS_i(b)$ of the model attenuation signal S(b; (p(i))) at a given b value to the parameter p(i) around the point $S_R(b; p_R(i))$. In fact all the expressions of $dS_i(b)$ that approach the analytical expression $$\frac{1}{S_R(b)} \cdot \frac{\partial S(b; (p(i)))}{\partial p(i)} (b; (p_R(i)))$$

will be appropriate.

Then, in a fourth step 18 a filtering of the NP key b values is carried out in order to decrease the number of acquired MRI images at different b values and to decrease therefore the MRI acquisition time.

To do so, a first filtering consists in removing the key b values that are associated to model parameters of low interest for the tissue type and/or the microstructure or biological state to characterize.

A second optional filtering consists in removing the key b values that provide the MRI signal with a sensitivity $dS_i(b)$ to the model parameters $p(i)$ around the reference signal $S_R(b)$ below a predetermined sensitivity threshold and/or that are higher than the validity range of the used generic attenuation model and/or which may results in values below a predetermined noise threshold level.

Thus, a subset of key b values is obtained that has a cardinality lower than or equal to NP.

As a particular case, the number of key $\underline{b}$ values forming the subset may be equal to the total number NP of model parameters.

As an example, the predetermined sensitivity threshold is equal to 1%.

Then, in the fifth step 20 a set of MRI images of a Field Of View (FOV) of the observed biological tissue is acquired by means of a motion-probing pulsed gradient MRI sequence programmed with gradient pulses configured to obtain the determined key $\underline{b}$ values of the subset.

Then in a sixth step 22 on a one-per-one voxel basis or on a predetermined Region Of Interest (ROI) including a set of voxels, a signature index is determined as a real number representative of the microstructure state and the type of the tissue present in the ROI or the voxel V, the signature index being a scalar function depending on the voxel signals acquired at the key b values of the subset.

It should be noted that regardless the kind of calculated signature index, calculating the signature index directly at ROI level is carried out by averaging the signals of all the voxels of the ROI for each key b value.

It should be noted that the scalar function defining the signature index depends directly on the voxel signals acquired at the key b value subset and does not use any generic attenuation model for the observed tissue.

As a first embodiment, when the key b value subset comprises only two key b values, a low key b value Lb, and a high key b value Hb, and following the ADC (Apparent Diffusion Coefficient) concept introduced in 1980's for Gaussian diffusion, a first kind of signature index of a voxel, designated by sADC(V), for "Synthetic ADC", is determined as:

$$sADC(V) = \text{Ln } [S_V(Lb)/S_V(Hb)]/(Hb-Lb) \qquad \text{Equation \#3}$$

where $S_V(Lb)$ designates the measured signal of the voxel for the MRI image acquired with the key b=Lb, and $S_V(Hb)$ designates the measured signal of the voxel for the MRI image acquired with the key b=Hb.

Since the key b values have been determined to provide the highest sensitivity to variations in the tissue features, this signature index sADC intrinsically encompasses several sensitive parameters of the generic attenuation model or even the model itself and is more sensitive and/or specific to the tissue features than the single ADC or $ADC_0$ values used in the generic IVIM/diffusion models. For instance, a very high signature index sADC obtained by using two very low key b values such that Hb=100 s/mm² and Lb=0 would specifically indicate the presence of flowing blood (hence a blood vessel). This example as illustrated later will show that the synthetic ADC (sADC) includes both the effects of Intra Voxel Incoherent Motion (IVIM) Gaussian and non-Gaussian components in the voxel signals.

As a second embodiment, a second kind of signature index, designated as Sdist is determined by calculating a pseudo-distance between the vector signal pattern observed at the key b values $b_k$ in the ROI or voxel $S_V(b_k)$ and the vector signal pattern calculated in the reference state tissue using the generic attenuation model $S_R(b_k)$, where k designates the integer rank of the key values of the subset. The pseudo-distance can be an algebraic distance, a correlation coefficient or a scalar product between $S_V(b_k)$ and $S_N(b_k)$ or any kind of distance. For example, the second signature index is defined as:

$$Sdist(V) = \sum_{b_k \in key\ b\ values} (-1)^{G(b_k)}[S_V(b_k) - S_R(b_k)]/S_R(b_k) \qquad \text{equation \#4}$$

where $G(b_k)$ can be even or odd depending on the sign of $dS(b_k)$, with $dS(b_k)=[S_V(b_k)-S_R(b_k)]/S_R(b_k)$.

For example, $G(b_k)$ is equal to 2 if $dS(b_k)>0$ and equal to 1 if $dS(b_k)<0$.

The value of Sdist which can be positive or negative provides quantitative information of the degree of deviation of the micro-structural or biological properties of the observed tissue with respect to the reference tissue.

Figure 2:
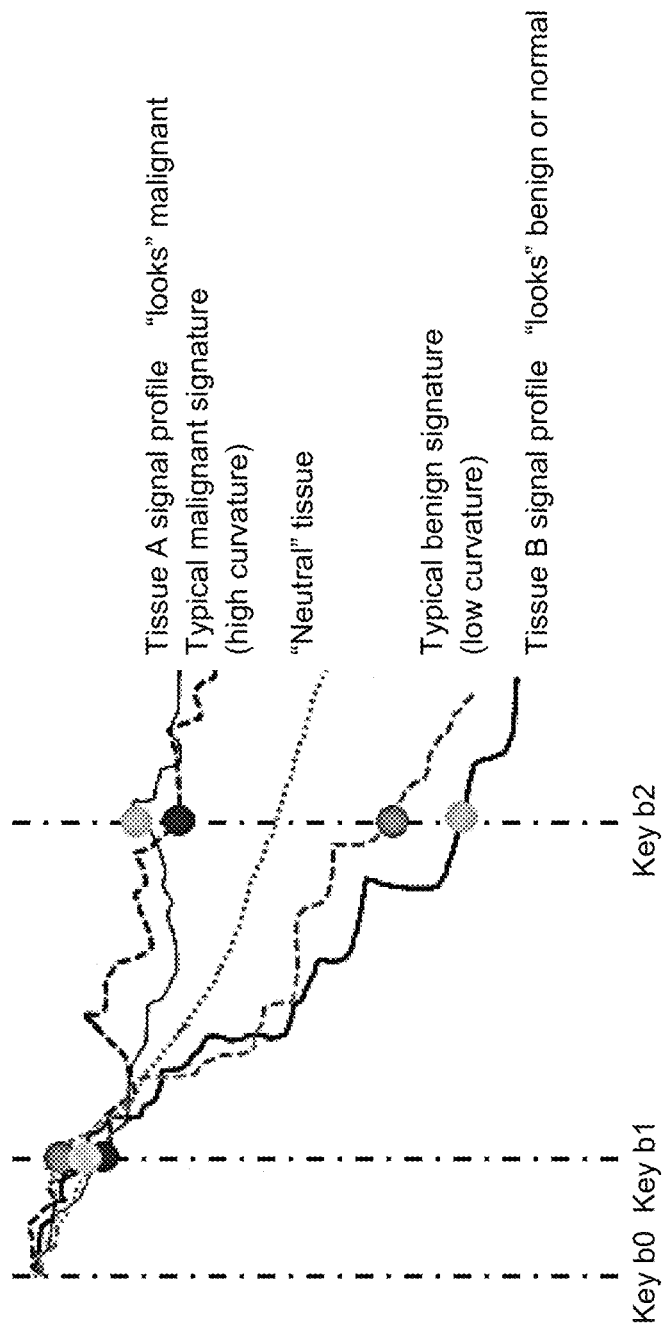
FIG. 2 is a geometrical view of the distances Sdist(V) separating a tissue signal V, a malignant tissue signal M, and a benign tissue signal B from a reference tissue signal R.

As illustrated in FIG. 2, the diffusion MRI signal of the observed tissue is directly compared to reference tissue signal profiles (e.g. "malignant" and "benign"). The proximity of the observed signal profile with either reference tissue allows a straightforward estimation of the nature of the observed tissue (eg "malignant" for Tissue A and "benign" for Tissue B). In order to quantify this "proximity" the distance index, Sdist as defined per equation #4, is calculated using signal profile values obtained at key b values.

One may also consider a set Rset of a number $\underline{r}$ of reference tissues Rj, j being an index identifying the reference tissue and ranging from 1 to $\underline{r}$ (i.e. the cardinality of Rset), each reference tissue Rj having its own parameter vector $(p_{Rj}(i))$ and a corresponding attenuated signal $S_{Rj}(b)$. A set of $\underline{r}$ signature distances Sdist(V; Rj) can then be calculated between the tissue under investigation and each reference tissue Rj as:

$$Sdist(V;Rj) = \Sigma_{b_{j,k} \in \{key\ b\ values\ de\ Rj\}} (-1)^{G(b_{j,k})}[S_V(b_{j,k}) - S_{Rj}(b_{j,k})]/S_{Rj}(b_{j,k})$$

Then, the tissue type or state of the tissue under investigation can be estimated as that of the reference tissue $Rj_0$ of Rset closest to the said tissue under investigation by using Sdist. Thus, $j_0$ is the reference tissue index defined by the equation:

$$Sdis(V;Rj_0) = \text{Min}_{j=1\ to\ r}(Sdist(V;R_j))$$

Thus a first extension of the second signature index Sdist as a pseudo-distance to a set R (of reference tissues Rj, designated by Sdistset(V; R), can be defined by the equation:

$$Sdistset(V;Rset) = \text{Min}_{j=1\ to\ r}(Sdis(V;R_j)) \qquad \text{Equation \#5}$$

Another second extension of the second signature index Sdist can be obtained by considering that MPG MRI signals are acquired in a tissue under a set C of different MPG conditions Cm, $\underline{m}$ being an index identifying the MPG condition and ranging from 1 to $\underline{c}$, $\underline{c}$ being the cardinality of the set C.

For instance, the conditions Cm are different orientations in space of the MPG pulses to take into account diffusion anisotropy and/or different diffusion times (defined by the time interval and the duration of the MPG) to take into account restricted diffusion effects.

The second extension of the second signature index Sdist, designated as SCdist is determined by calculating any kind of pseudo-distance between an 2D-array signal pattern $S_V(b_{k(m)},Cm)$ observed at different key b values $b_{k(m)}$ under different conditions in the ROI or voxel and the 2-D-array signal pattern $S_R(b_{k(m)},Cm)$, measured or calculated in a reference state tissue R using a generic attenuation model $S_{R(Cm)}(b_{k(m)})$, where k(m) designates the integer rank of the key b values of the subset corresponding to the condition Cm.

For example, the second signature index is defined as:

$$SCdist(V;R) = \sum_{m=1 \text{ to } c;} \sum_{b_k(m) \in key\ b\ values} (-1)^{G(b_k(m),Cm)} [ \qquad \text{equation \#6}$$

$$S_V(b_k(m), Cm) - S_R(b_k(m), Cm)]/S_R(b_k(m), Cm)$$

where $G(b_{k(m)},Cm)$ is an integer that can be even or odd depending on the sign of $[S_V(b_k(m),Cm)-S_R(b_k(m),Cm)]/S_R(b_k(m),Cm)$.

One may also consider a set Rset of a number $\underline{r}$ of reference tissues Rj, j being an index identifying the reference tissue and ranging from 1 to $\underline{r}$ (i.e. the cardinality of Rset), each reference tissue Rj having its own 2D-array signal pattern $S_{Rj}(b_{k(m)},Cm)$. A set of $\underline{r}$ signature distances SCdist(V; Rj) can then be calculated between the tissue under investigation and each reference tissue Rj as:

$$SCdist(V;Rj) = \sum_{m=1 \text{ to } c;} \sum_{b_k(m) \in key\ b\ values(m)} (-1)^{G(b_k(m),Cm)}$$

$$[S_V(b_k(m), Cm) - S_{Rj}(b_k(m), Cm)]/S_{Rj}(b_k(m), Cm)$$

Then, the tissue type or state of the tissue under investigation can be estimated as that of the reference tissue $Rj_0$ of Rset closest to the said tissue under investigation by using SCdist. Thus, $j_0$ is the reference tissue index defined by the equation:

$$SCdis(V;Rj_0)=\text{Min}_{j=1\ to\ r}(SCdist(V;R_j))$$

Thus, a third extension of the second signature index Sdist as a third pseudo-distance to the set Rset of reference tissues Rj, designated by SCdistset(V; Rset), can be defined by the equation:

$$SCdistset(V;R)=\text{Min}_{j=1\ to\ r}(SCdis(V;R_j)) \qquad \text{equation \#7}$$

It should be noted that the subset of key $\underline{b}$ values may be different for each acquisition condition Cm.

Figure 3:
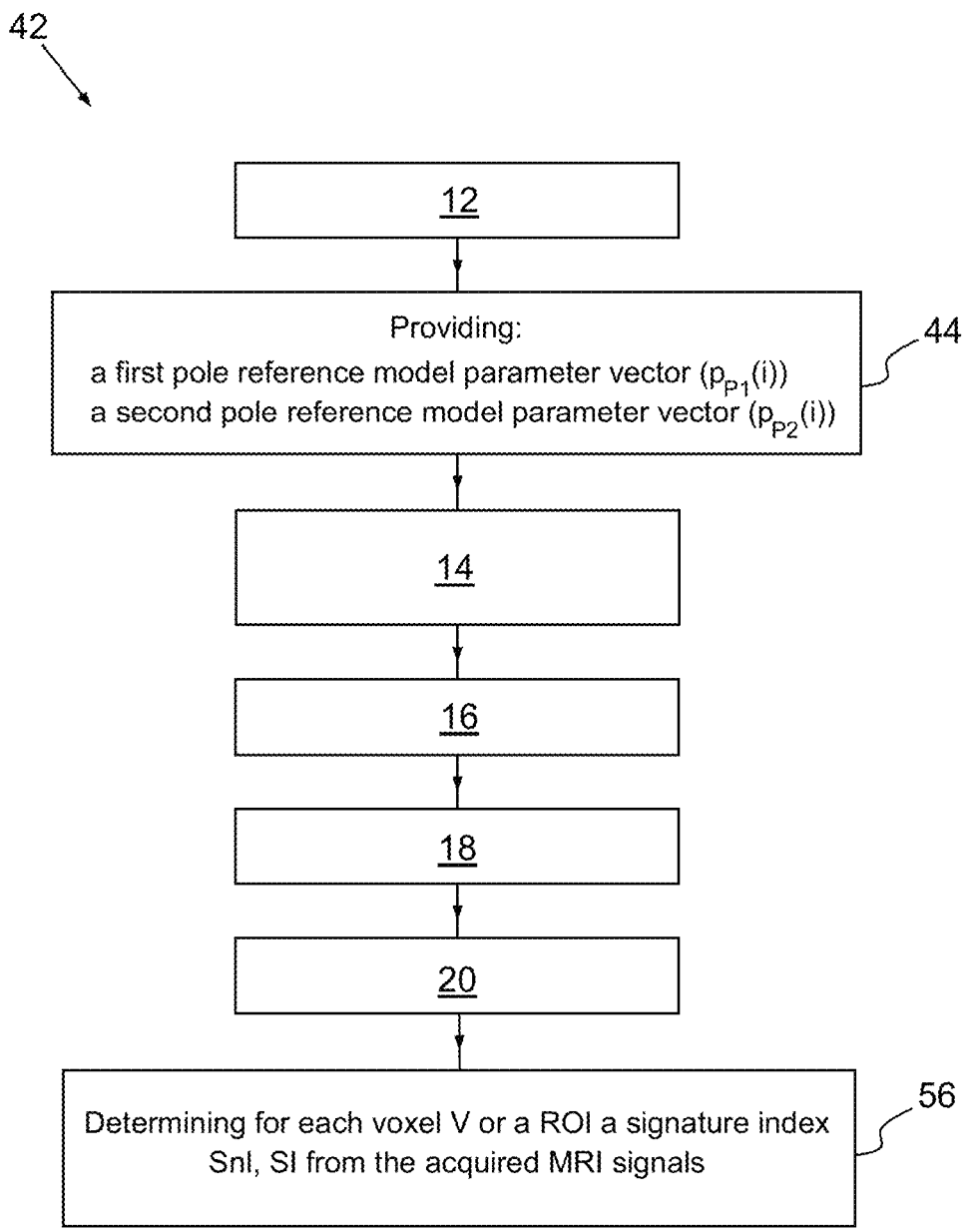
FIG. 3 is a flow chart of a first variant of the method illustrated in the FIG. 1.

According to FIG. 3 and a first variant 42 of the above method of FIG. 1, when two reference tissues are considered, a third kind of signature index, designated as Snl, is defined to normalize the pseudo-distance based signature index, i.e. the second kind signature distance Sdist. To do so, two calibrating or pole states P1, P2 of tissue of interest are provided around a neutral reference state given with its parameter vector $(p_N(i))$, and they are associated with a first pole reference model parameter vector $(p_{P1}(i))$ and a second pole reference parameter vector $(p_{P2}(i))$. These two calibrating states P1, P2 are provided as shown in FIG. 2 in a supplemental seventh step 44 inserted between the first step 12 and the second step 14.

For example, the first calibrating state P1 of the tissue to the second calibrating state P2 correspond to a "benign" versus a "malign" tissue for a tumor tissue, or a tissue "under medical treatment" versus an "untreated" tissue, or a "resting" versus an "activated" tissue, or a "normal" versus an "inflammatory" tissue, or a tissue with "first spatial orientation" versus a tissue with a "second spatial orientation" for an anisotropic tissue such as in muscles, the heart or brain white matter tissue, or a tissue with a "first kind of cyto architectony" versus a "second kind of cyto architectony" for a brain cortex tissue.

More generally and depending on the question to be addressed, the first calibrating state P1 characterizes a biological property at a higher degree while the second calibrating states P2 characterizes the biological property at a lower degree.

The two pole reference parameter vectors, $(p_{P1}(i))$ and $(p_{P2}(i))$, are obtained once for all from preliminary MRI images of similar tissue states acquired in a preliminary step of calibration and using the generic attenuation model, or from previously established values from the literature, the first pole and second pole states P1, P2 as well as their corresponding reference model parameter vectors, $(p_{P1}(i))$ and $(p_{P2}(i))$, being significantly different.

Figure 4:
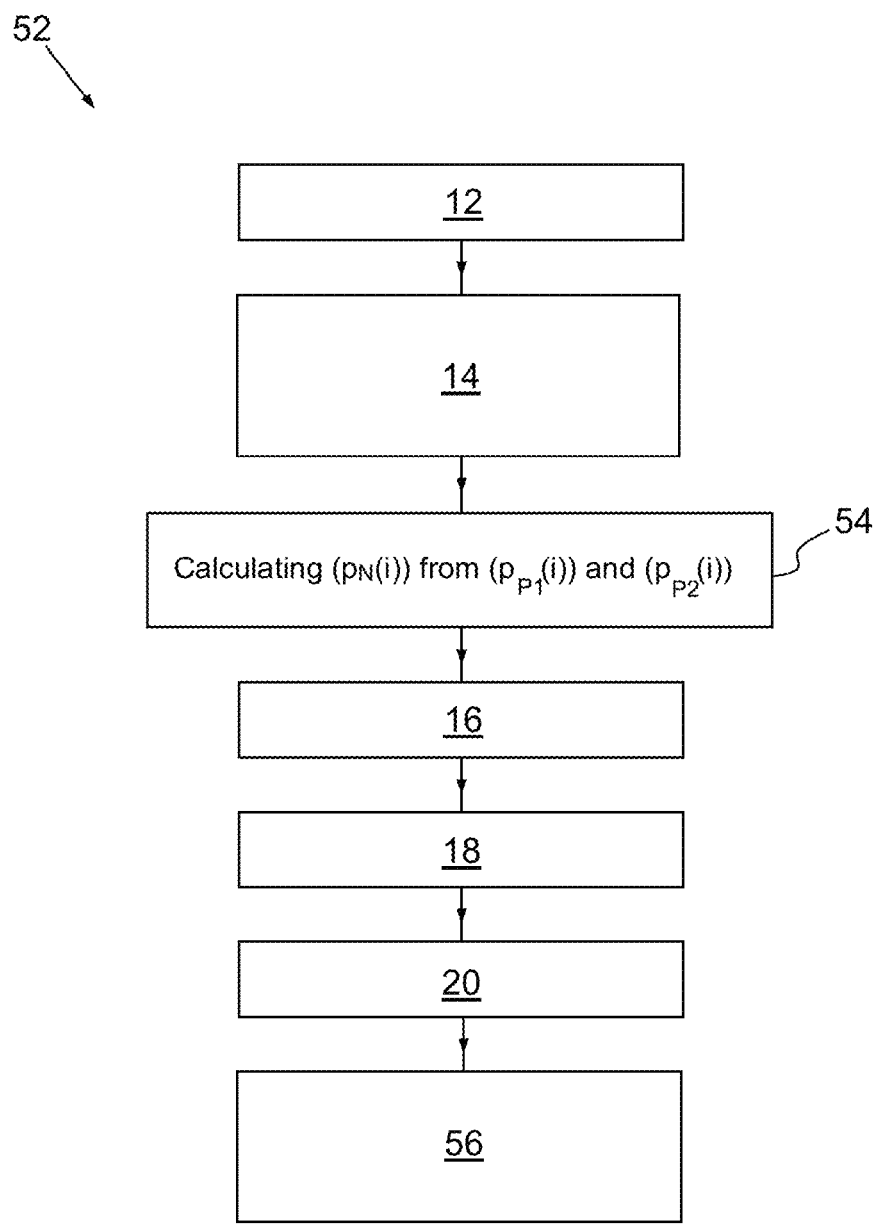
FIG. 4 is a flow chart of a second variant of the method illustrated in the FIG. 1 derived from the first variant method of FIG. 3.

According to FIG. 4, a second variant 52 of the method 2 of FIG. 1 and a first variant 52 of the method 42 of FIG. 3, if the neutral reference model parameter vector $(p_N(i))$ cannot be determined from acquired images, in a eighth step 54 replacing the second step 14 of FIG. 3, this vector is calculated as the average of the first pole reference model parameter vector $(p_{P1}(i))$ and the second pole reference parameter vector $(p_{P2}(i))$.

The reference second kind signature index is then calculated once for all for each pole reference model parameter vector $(p_{P1}(i))$ and $(p_{P2}(i))$, respectively designated as Sdist1 and Sdist2 using the neutral tissue as the reference tissue. These two signature indices are located around zero on the real axis, the zero value corresponding to the neutral reference tissue vector.

In both FIGS. 3 and 4, as a variant step 56 of the step 22 of FIG. 1, a third kind of signature index designated as a normalized signature index Snl for a ROI or a voxel of the tissue under investigation, can be then obtained by comparing the second kind signature index of the voxel Sdist(V) with those of the references, Sdist1 and Sdist2. The third kind signature index Snl will provide quantitative information on the "proximity" of the tissue under investigation with either first calibration tissue P1 or second calibration tissue P2. For instance, the third signature index Snl(V) may be defined as:

$$Snl(V)=\{\max([Sdist(V)/Sdist1],0)-[\max([Sdist(V)/Sdist2],0)\} \qquad \text{equation \#8}$$

This normalized signature index Snl is equal to zero when the state of the voxel is the neutral state, and has opposite signs when the tissue resembles the first and second calibrating microstructure states. If the tissue voxel IVIM/non-Gaussian diffusion MRI pattern is very similar to the first pole state P1, its normalized signature index is equal to +1 while, if the tissue voxel pattern is very similar to the second pole state P2, its normalized signature index Snl is equal to −1. A normalized signature Snl greater than +1 means that the features (i.e. microstructure, biological property, etc.) owned by the tissue under investigation are more pronounced than ones owned by the first pole state tissue P1. Reciprocally, a normalized signature index Snl lower than −1 means that the features (i.e. microstructure, biological property, etc.) owned by the tissue under investigation are more pronounced than ones owned by the second pole state tissue P2. A normalized signature index Snl comprised between −1 and +1 means that the tissue under investigation only partially shares the features of the first pole state tissue P1 if positive, or the second pole state tissue P2 if negative.

As a fourth embodiment, an absolute index designated by SI is determined by scaling, linearly or not linearly, the normalized signature index Snl. As an example, in order to provide a linear global SI centered around 50 for the neutral state, 75 for the first pole state P1 and 25 for the second pole state P2, the fourth signature index is expressed as:

$$SI=(Snl+1)*25+25 \quad \text{equation \#9}$$

A scaled normalized signature index SI greater than 75 means that that the features (i.e. microstructure, biological property, etc.) owned by the tissue under investigation are more pronounced than ones owned by the first pole state tissue P1.

Reciprocally, a scaled normalized signature index SI lower than 25 means that the features (i.e. microstructure, biological property, etc.) owned by the tissue under investigation are more pronounced than ones owned by the second pole state tissue P2. A scaled normalized signature index SI comprised between 25 and 75 means that the tissue under investigation only partially shares the features of the first pole state tissue P1 if greater than 50, or the second pole state tissue P2 if lower than 50.

Figure 5:
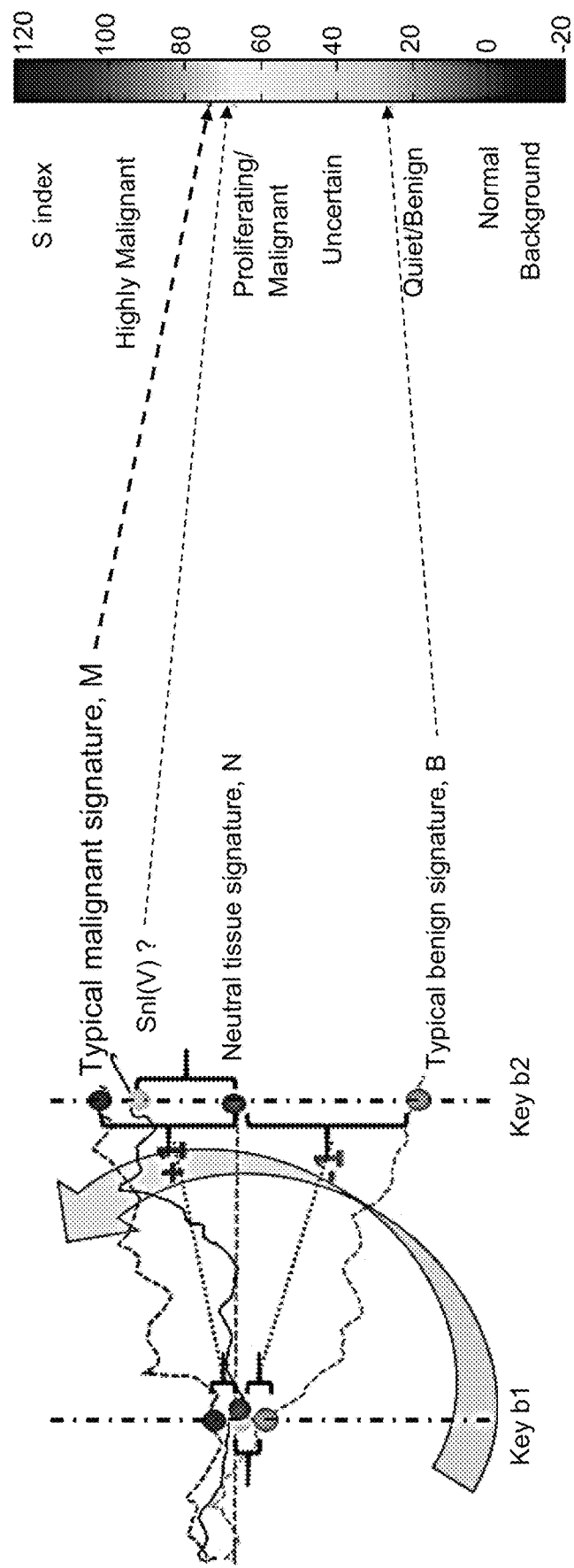
FIG. 5 is a geometrical view of the distance Snl(V) separating a tissue signal V, a malignant tissue signal M, and a benign tissue signal B from a reference tissue signal R.

As illustrated in FIG. 5, the distance index Sdist can be further refined through a normalization process. By rotating the signal profiles from FIG. 2 so that the signal profile from the neutral tissue becomes flat (horizontal) one can easily see that "malignant" tissues now appear with an increasing signal profile, while "benign" tissues appear with a decreased signal profile. By normalizing distances to +1 for typical malignant tissues and −1 for typical benign tissues one obtain an absolute scale index, Snl, to classify observed tissues. For convenience, Snl can further be rescaled, as an Sindex, for instance between 25 and 75 for benign and malignant lesions, respectively. Malignant lesions will appear with a Sindex above 50, while benign lesions will have a Sindex below 50. Lesions with a Sindex far above 50 will be highly malignant, while tissues with very low Sindex, below 25, will reflect normal tissues.

The type of tissue is a tissue of the organs consisting of the brain, head and neck organs, breast, prostate, liver, pancreas, lung, heart, muscle or joints.

The type of states may refer to a lesional tissue versus a normal tissue, a a "benign" versus a "malign" tissue for a tumor tissue, or a tissue "under medical treatment" versus an "untreated" tissue, or a "resting" versus an "activated" tissue, or a "normal" versus an "inflammatory" tissue, or a tissue with a "first spatial orientation" versus a tissue with a "second spatial orientation" for an anisotropic tissue such as in muscles, the heart or brain white matter tissue, or a tissue with a "first kind of cyto architectony" versus a "second kind of cyto architectony" for a brain cortex tissue.

An important advantage of the above described signature indices is that these indices are calculated regardless of the attenuation model and do not require the estimation of any model parameters. The generic models are used only to establish the key b values and the signal values for the reference and state tissues at those key b values. Any attenuation model giving a good account of the signal dependence on the key b values that take into account IVIM and non-Gaussian diffusion effects would suffice.

According to a first application of the MRI method 2, 42, 45, illustrated in FIGS. 1, 3 and 4, a breast tissue is considered, the generic attenuation model is an IVIM/Kurtosis model as described in the second article of lima M. et al. (Ref.#4).

The model function f1(x) describing the signal attenuation is expressed by the equation as:

$$S(b)=[s_0^2\{f_{IVIM}\exp(-b\cdot D^*)+(1-f_{IVIM})\exp[-b\cdot ADC_0+ (b\cdot ADC_0)^2 K/6]\}^2+NCF]^{1/2} \quad \text{Equation \#10}$$

where $S_0$ is the signal acquired with no diffusion weighting for b equal to zero,
$f_{IVIM}$ is the volume fraction of incoherently flowing blood in the tissue,
D* is the pseudo-diffusion coefficient associated to the IVIM effect,
$ADC_0$ is the virtual Apparent Diffusion Coefficient which would be obtained when b approaches 0,
K is the kurtosis parameter K, and
NCF is a fixed Noise Correction Factor.

As an example and by using typical values for fIVIM, ADCo, K and D* for malignant and benign lesions in breast cancer from the here below Table 1 described in the above related cited article from lima et al., the respective contribution of those parameters on the overall attenuation signal were evaluated for each degree of diffusion sensitization by varying the b value over a predetermined range.

TABLE 1

|  | fIVIM (%) | D* ($10^{-3}$ mm²/s) | ADCo ($10^{-3}$ mm²/s) | K |
|---|---|---|---|---|
| Malignant Tissue | 8 | 11 | 1.1 | .9 |
| Benign Tissue | 4 | 10 | 2.0 | .6 |
| "Neutral" Tissue | 6 | 10 | 1.4 | .75 |

Figure 6A:
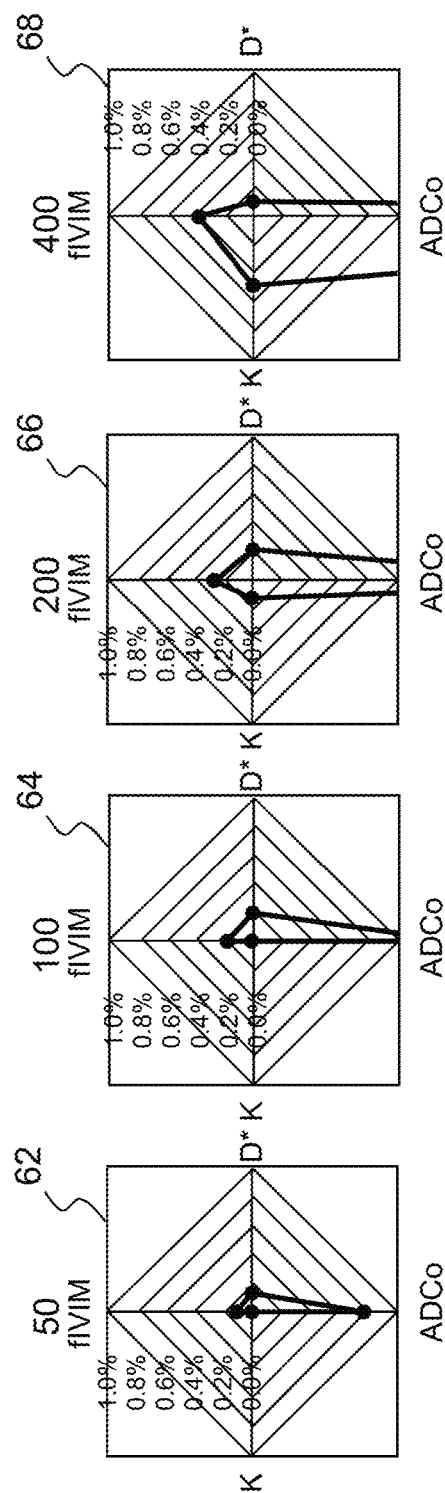
FIGS. 6A and 6B are views of the relative contributions of the IVIM/Kurtosis model parameters $f_{IVIM}$, D*, ADC0 and K to global signal variations for several b values (50, 100, 200, 400, 800, 1600, 2400, 3400 sec/mm$^2$) when varying these parameters by 10% around the model parameter corresponding to a virtual neutral breast human tumor tissue.
Figure 6B:
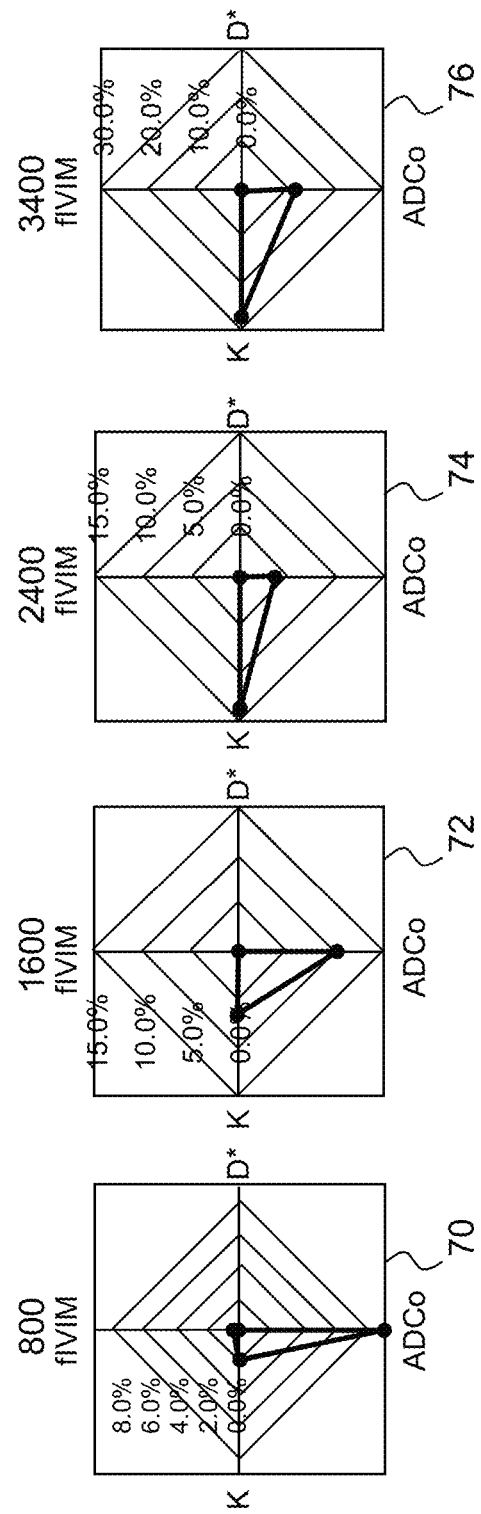

According to the FIGS. 6A and 6B, views 62, 64, 66, 68, 70, 72, 74, 76 of the relative contributions $dS_i(b)$ of the model parameters $f_{IVIM}$, D*, ADC0 and K to global signal variations of attenuation signal SN(b) are illustrated for several respective b values 50, 100, 200, 400, 800, 1600, 2400, 3400 when varying these parameters by 10% around the model parameters corresponding to a virtual neutral breast human tumoral tissue. The FIGS. 6A-6B show that the relative contribution to the signal of each parameter strongly depends on the b values, as expected from the Equation #10, but with a specific b value sensitivity illustrated by four points located each on a grid of sensitivity and a different abscissa semi-axis associated to one model parameter amongst $f_{IVIM}$, D*, ADCo and K. For instance, the most sensitive b values for fIVIM, D*, ADCo and K are 400, 200, 800 and 3400 s/mm², respectively.

Figure 7A:
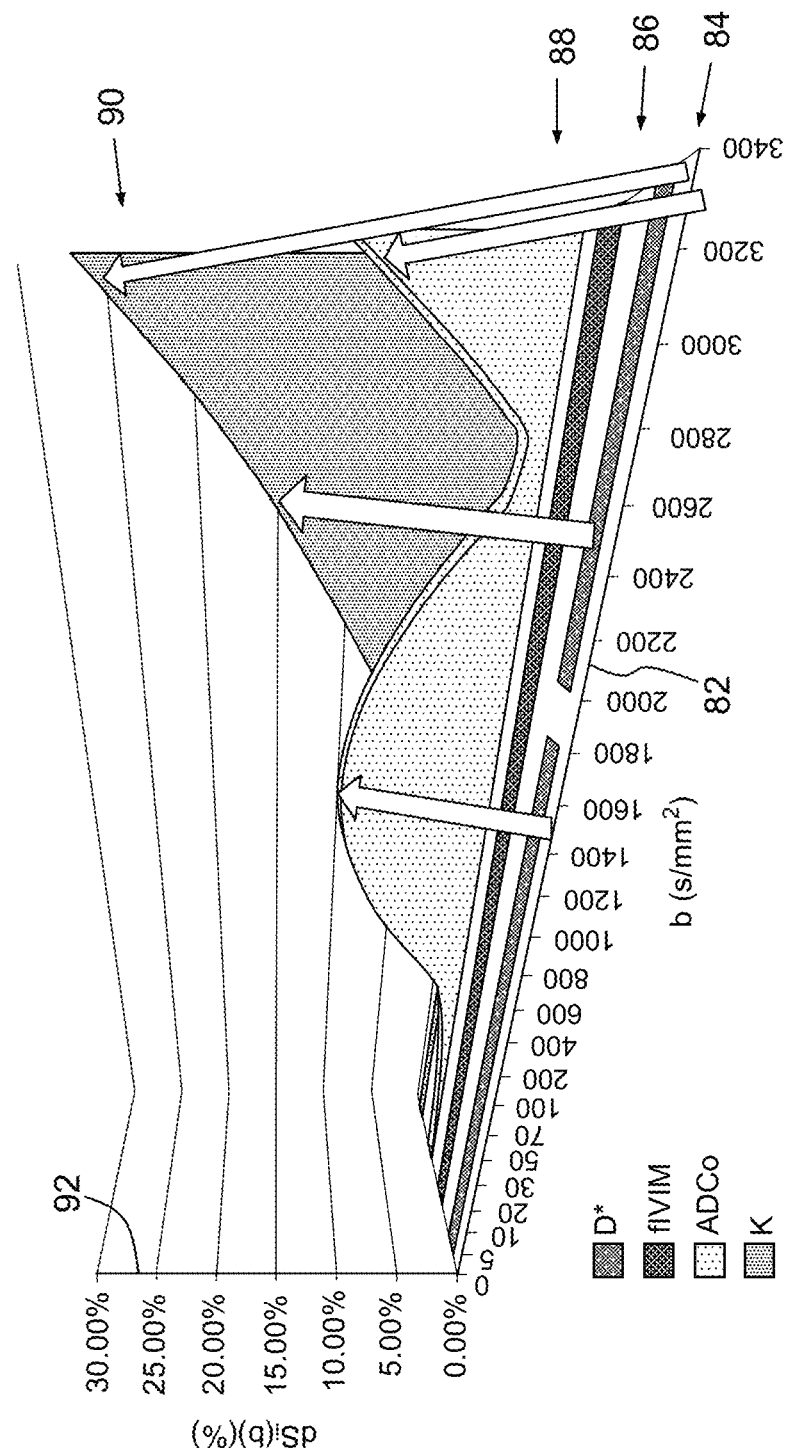
FIGS. 7A and 7B are views of the evolution of the partial differential sensitivity of the overall IVIM/diffusion signal to each model parameter $f_{IVIM}$, D*, ADC0 and K versus the b value, when varying the model parameters by 10% around the same model parameters corresponding to a virtual neutral breast human tumor tissue as for the FIGS. 6A and 6B.
Figure 7B:
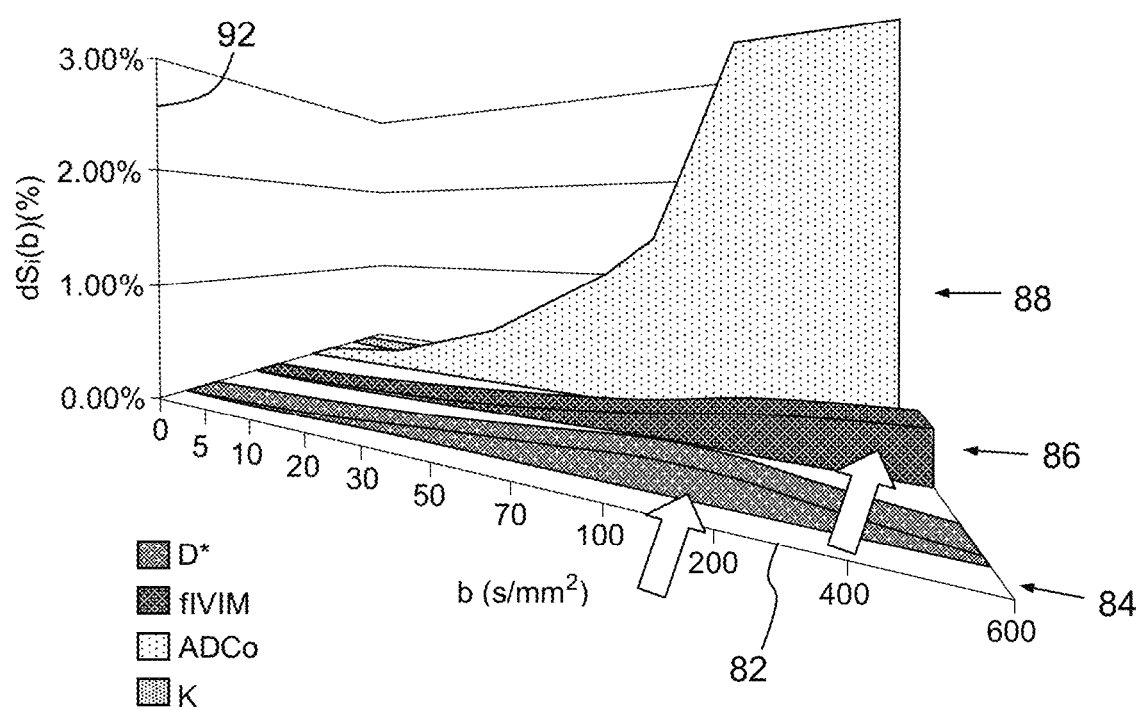

According to the FIGS. 7A-7B, it is shown the evolution of the differential sensitivity $dS_i(b)$ of the overall IVIM/diffusion signal to each model parameter, D*, $f_{IVIM}$, ADC0 and K versus the b value, when varying the model parameters by 10% around the same model parameters corresponding to a virtual neutral breast human tumoral tissue as same used in the FIGS. 6A and 6B. In the FIG. 7A, the b value is drawn on an abscissa axis 82 and is varied over a range interval [0, 3400 s/mm²] and the contributions of the different model parameters D*, $f_{IVIM}$, ADC0 and K expressed in percentage are shown in perspective on different respective slices 84, 86, 88, 90 by using a same ordinate axis 94. The FIG. 7B is the zoom of the FIG. 7A when the b value is varied over the range interval [0, 600 s/mm²].

From the FIGS. 7A and 7B one can see that the b values between 1600 and 2400 are good candidates as key b values for detecting both significant contributions of ADCo and K. It also appears that variations in ADCo and K have a much greater impact on the overall signal than fIVIM and D*, suggesting that diffusion has potentially a greater diagnostic value than IVIM.

Based on this differential sensitivity, one may consider that some b values, called "key b values", can be found to maximize sensitivity to IVIM/diffusion parameters, hence to best distinguish tissues, assuming they have different sets of IVIM/diffusion parameter values.

A first list of candidate key b values can be built and illustrated by the large arrows drawn on the FIGS. 7A and 7B.

Figure 8:
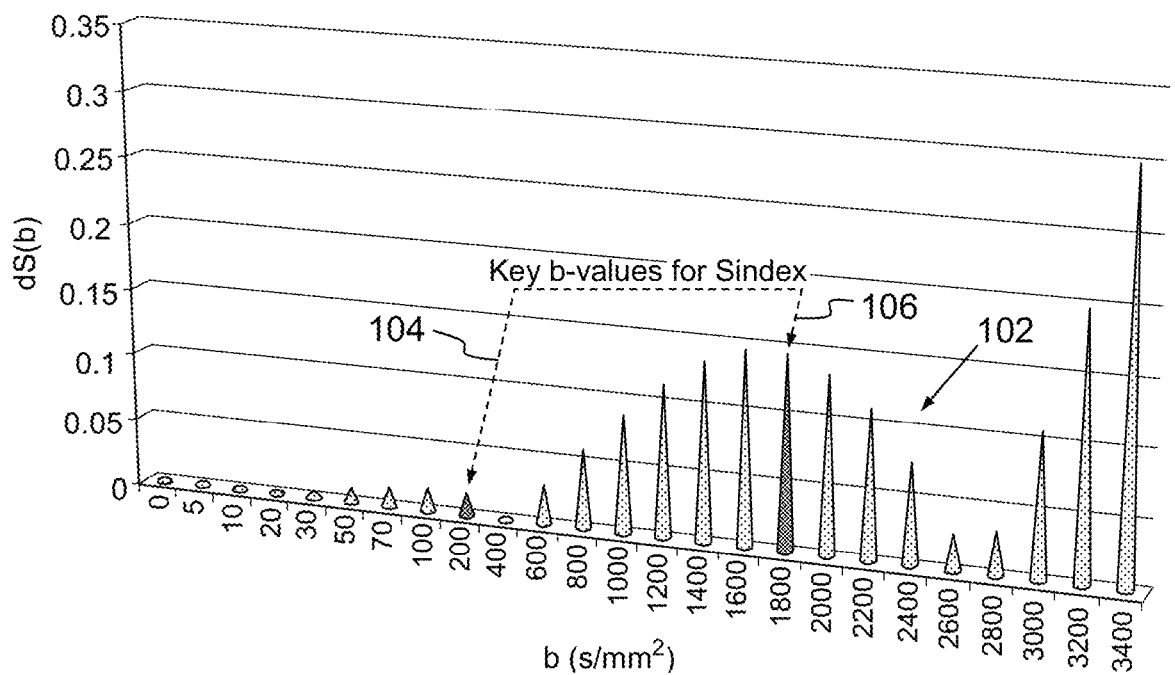
FIG. 8 is a view of an exemplary selection of the key b values based on the sensitivity results illustrated on the FIGS. 6A-6B and 7A-7B when using a method of FIG. 4, the key b values being selected to provide the best sensitivity of the acquired overall MRI signal when varying the parameters $f_{IVIM}$, D*, ADC0 and K by 10% around the model parameter corresponding to a virtual neutral (or uncertain) breast tumor tissue.

Using data from Table 1 as an example and a synthesized illustration in FIG. 8 of the sensitivity evolution 102 of the overall attenuation signal to all the model parameters versus the b values, a discrete narrow size set of key b values can be identified. Around 100-200 s/mm$^2$, one "low" key b value, designated by Lb, may be used for IVIM, while around 1400-1800 s/mm$^2$ "high" key b values, designated by Hb, may be used for non-Gaussian diffusion. It should be noted that a b value above 3400 s/mm$^2$ also has a strong tissue differentiation potential, but signal acquired at such high b values generally become very low with typical commercial MRI scanners. The Kurtosis model described the equation #10 is also known to fail at very high b values. In addition, some b values, 0 and 400 s/mm$^2$ for example appear as completely insensitive to the tissue states.

In summary, differentiation of tissue states, in regard to differentiating the degree of a property, here the malignity, of a type of tissue, here a breast human tumor tissue, can be obtained from a very small set of b values (2 or three key b values), as compared to, for instance, 16 b values as reported in the above cited second article of lima M. et al. (Ref.#4) wherein the IVIM/diffusion parameters have to be evaluated, which is not the case with the method of the invention.

As a result, a dramatic shortening of the acquisition time can be obtained, which is an important concern for clinical protocols, especially in the case of non-cooperative patients.

As an example from FIG. 8, the two selected key b values, designated respectively by the numeral references 104 and 106, are equal to 200 and 1500 s/mm$^2$.

Once the key b values have been identified, typical signals, $S_M(b)$, $S_B(b)$ and $S_N(b)$ can be calculated once for all by using the data of Table 1 and the equation #10 of the attenuation model for each signal typical state M, S, N designating Malignant tumor tissue, Benign tumor Tissue, as well as signal differences, $dS_{M,B}(b)=[S_{M,B}(b)-S_N(b)]/S_N(b)$ between malignant, $S_M$, and benign, $S_B$, tissue signals, and the virtual "neutral" tissue signal, $S_N$. As malignant lesions are characterized by higher fIVIM, lower ADCo and higher K values, in an opposite way to benign lesions characterized by lower fIVIM, higher ADCo and lower K values (effect contribution of K higher than effect contribution of ADCo,) one expects $dS_M>0$ and $dS_B<0$.

The normalized signature index, $SnI(V)$, can be defined here for a signal, $S_V$, measured in the observed tissue as:

$$SIn(V) = \begin{Bmatrix} \max([dS_V(Hb) - dS_V(Lb)]/[dS_M(Hb) - dS_M(Lb)], 0) \\ -[\max([dS_V(Hb) - dS_V(Lb)]/[dS_B(Hb) - dS_B(Lb)], 0) \end{Bmatrix} \quad \text{equation #11}$$

where the tissue signal, $S_V(b)$, has been normalized to 1 by division with $S_V(0)$, and $dS_V(b)=[S_V(b)-S_N(b)]/S_N(b)$.

It should be noted that $[dS_X(Hb)-dS_X(Lb)]$ with X=V, M or B also represents the second kind signature index Sdist (X) for the tissue X.

For malignant tumor tissues Sin is higher than 0, in particular SIn=1 for the typical malignant tissue M of Table 1, while SnI is lower than 0 for benign tumor tissues, in particular SnI=−1 for the typical benign tissue B of Table 1. The normalized signature index SIn is equal to 0 for a neutral (undetermined) tumor tissue.

Figure 9:
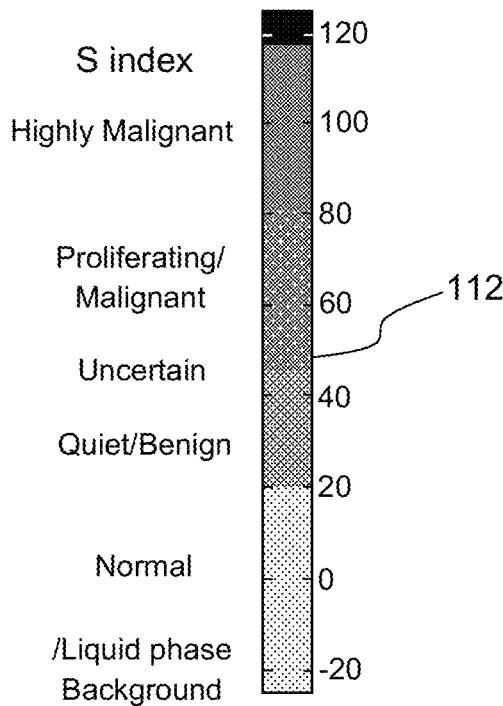
FIG. 9 is view of the linear scaling of a normalized signature index Snl as an absolute signature index SI.

As shown in FIG. 9, the third normalized signature index SIn can further be linearly scaled as the fourth kind signature index, SI, defined by the expression: SI=(SI+1)*25+25, so that SI is centered at 50 for a virtual neutral tumor tissue N, SI=75 for a typical malignant tumor tissue M and SI=25 for a typical benign tumor tissue. For normal tissues i.e without tumor lesions, SI is comprised between 0-20, even below 0 for liquids in cystic lesions or breast canals, while in very malignant tissues SI can be much higher than 100.

From the data results of the above cited article from lima M. et al. (Ref.#4), it has been found that the average SI was found to be 76±34 in malignant lesions and 31±34 in benign lesions.

As a second application and validation of the method of the invention, the same IVIM/kurtosis model as one used in the case of human breast tumor lesions has been used in the case of human head and neck tumors, using the same model parameters of the typical attenuated signals corresponding to a malignant tumor tissue (M), a benign tumor tissue (B), a virtual neutral tissue (N), leading to the same key b values. These data are extracted from a third article from lima M. et al. to be published and presented at the next ISMSM Conference of June 2015. The overall performance (AUC) of S-index for this study was is 0.89 (sensitivity 88.9%, specificity 84.2%; PPV (i.e. Positive Predictive Value) 88.9% and NPV (i.e. Negative Predictive Value) 84.2%, higher than AUC for ADC$_0$, K, fIVIM (0.85; 0.83; 0.58 respectively).

As a third application and validation of the method of the invention, the same IVIM/kurtosis model as one used in the case of human breast tumor lesions has been used in the case of rat brain tumor data, but based on different data concerning the model parameters of the typical attenuated signals corresponding to a malignant tumor tissue (M), a benign tumor tissue (B), a virtual neutral tissue (N). These data are extracted from the first article from lima M. et al. (Ref.#3). By using these data, the table 1 is replaced by the following table 2:

TABLE 2

|  | fIVIM (%) | D* ($10^{-3}$ mm$^2$/s) | ADCo ($10^{-3}$ mm$^2$/s) | K |
|---|---|---|---|---|
| Malignant Tissue | 4 | 11 | 0.7 | 1.1 |
| Benign Tissue | 0 | 11 | 0.1 | 0.65 |
| "Neutral" Tissue | 2 | 11 | 0.85 | 0.8 |

Based on these new data the two key b values are here equal to 200 s/mm$_2$ for the low key b value Lb and t 1600 s/mm$^2$ for the high key b value Hb. Similarly to the case of the human breast tumor tissue, the typical signals $S_M(b)$, $S_B(b)$ and $S_N(b)$ can be calculated once for all by using the data of Table 2 and the equation #10 of the attenuation model.

Figure 11:
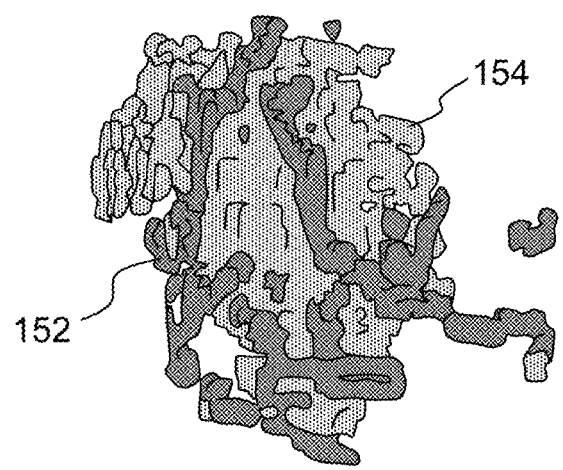
FIG. 11 is a view of an IVIM angiogram of a human breast normal tissue by using a signature index sADC or Snl as determined by the method of FIGS. 1, 3 and 4.

Then, using only the signal (at voxel or ROI level) acquired at the two key b values, Lb and Hb, an absolute signature index SI can be derived which gives an indication on the tissue nature and displayed according to a color scale 132 and in colored maps 134, 136, 138, 140, 142, 144 as shown in FIG. 11. The scalar signature index SI reflects the "proximity" of the lesion signal to the signal pattern of typical or reference tissues (e.g. malignant, benign, liquid, etc.) in light of a degree of a property or a feature owned by these reference tissues.

Figure 10:
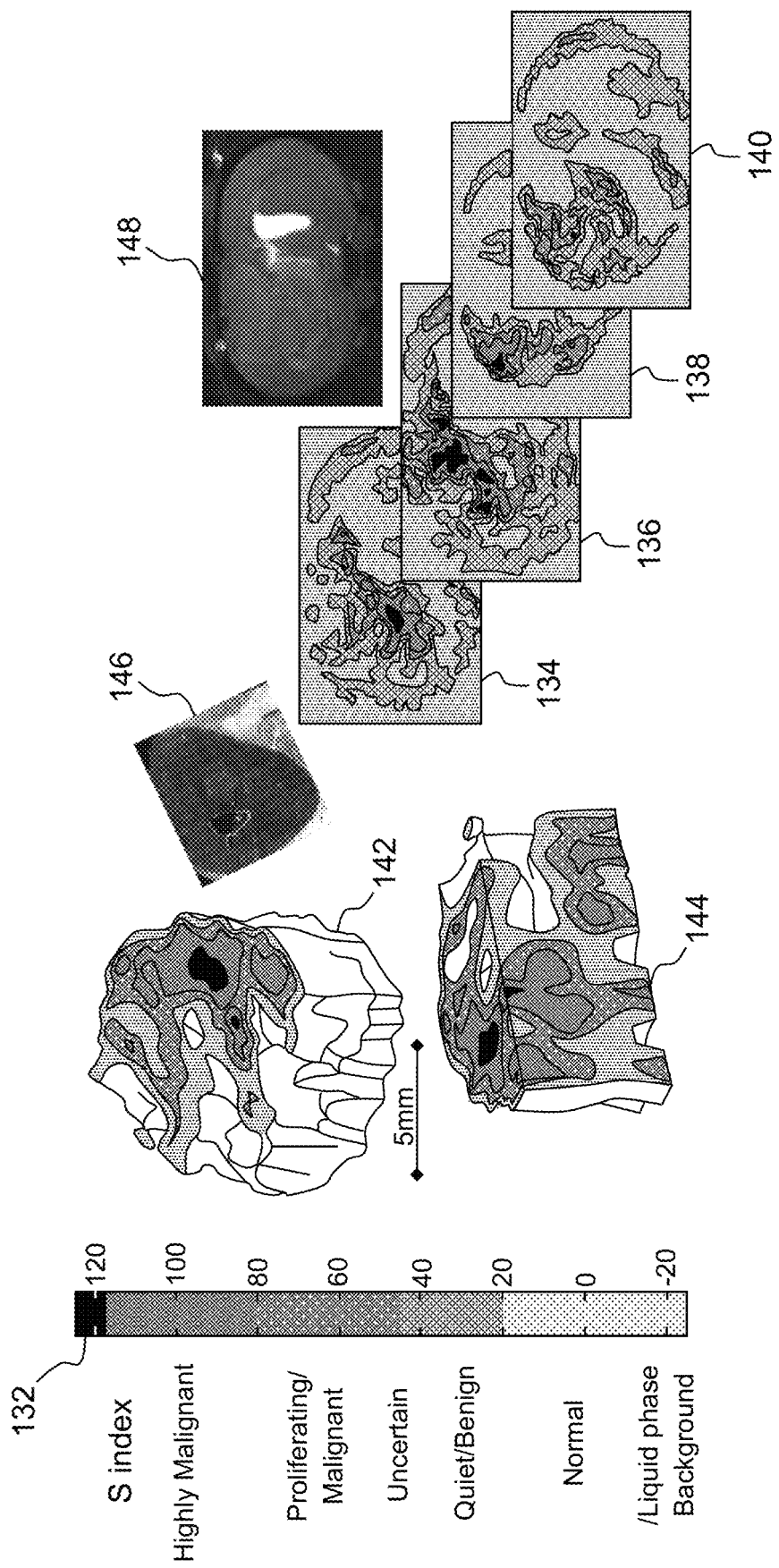
FIG. 10 is a view of reconstructed 2D slices and 3D volume SI MR images of a rat brain tumor tissue when using the method of FIG. 4 with an IVIM/Kurtosis model.

According to FIG. 10, the four exemplary SI maps 134, 136, 138, 140 as four slices and the corresponding 3D rendering 142, 144 shows tumor heterogeneity in a rat brain 9L glioma tumor model. T2W slice 146 and histological cut 148 (CD31 stain) are shown for reference.

More generally when the used model is an IVIM/kurtosis model and when the set of key b values has a cardinality equal to 2 and includes a lower key b value Lb and a higher key b value Hb, a normalized signature index Snl of a voxel Snl(V) is calculated according to the expression:

$$Snl(V) = \begin{Bmatrix} \max([dS_V(Hb) - dS_V(Lb)] / [dS_{P1}(Hb) - dS_{P1}(Lb)], 0) \\ -[\max([dS_V(Hb) - dS_V(Lb)] / [dS_{P2}(Hb) - dS_{P2}(Lb)], 0)] \end{Bmatrix} \quad \text{equation \#12}$$

with $$dS_X(b) = [S_X(b) - S_N(b)] / S_N(b)$$

For X=V, P1, P2 and for b=Hb, Lb, $S_{P1}(b)$, $SP_{P2}(b)$, $S_N(b)$ being the signals corresponding respectively to a first actual state P1, a second actual state P2, and a neutral state previously identified by the model and their respective first pole reference model parameter vector $(p_{P1}(i))$, second pole reference parameter vector $(p_{P2}(i))$, and neutral reference model parameter vector $(p_N(i))$ so that the signals values $S_{P1}(Lb)$, $S_{P2}(Lb)$, $S_N(Lb)$, $S_{P1}(Hb)$, $S_{P2}(Hb)$, $S_N(Hb)$ can be calculated, and where $S_V(Lb)$ designates the measured signal of the voxel for the MRI image acquired with the low key b value Lb, and $S_V(Hb)$ designates the measured signal of the voxel for the MRI image acquired with the high key b value Hb.

The normalized signature index Snl can be scaled, linearly or not by a calibration function to provide an absolute signature index SI. As an example, in order to provide a linear global SI centered around 50 for the neutral state, 75 for the first pole state P1 and 25 for the second pole state, the fourth signature index is expressed as:

SI=(Snl+1)*25+25

A signature index greater than 75 means that that the features (i.e. microstructure, biological property, etc.) owned by the tissue under investigation are more pronounced than ones owned by the first pole state tissue P1.

Reciprocally, a scaled normalized signature index SI lower than 25 means that the features (i.e. microstructure, biological property, etc.) owned by the tissue under investigation are more pronounced than ones owned by the second pole state tissue P2. A scaled normalized signature index SI comprised between 25 and 75 means that the tissue under investigation only partially shares the features of the first pole state tissue P1 if greater than 50, or the second pole state tissue P2 if lower than 50.

In practice, the normalized signature index Snl or the absolute signature index SI can be obtained at voxel level or within a manually or automatically drawn Region-of-Interest (ROI). At ROI level statistics on Snl or SI can also be derived using histograms (for instance, mean and standard-deviation within the lesion, giving information of lesion malignancy and heterogeneity, skewness and kurtosis, malignant charge taking into account the lesion volume with SI>50), as shown in the third article of lima et al. to be published. Color-encoded maps and 3D renderings of the lesions based on the voxel-by-voxel Sindex can also be generated for a better view of lesion conspicuity and heterogeneity, or provide spatial guidance for biopsy sites.

The invention only needs a very limited set of "key' images optimized for sensitivity to tissue features, which also results in very short acquisition time. Furthermore, acceleration is also obtained during data processing as signal time profiles are not matched with a large database of signals to retrieve parameter estimates but as the few "pole reference" image signals are matched with those of few typical tissues, without the need to estimate diffusion parameters.

Oppositely to current approaches based on full fitting of MRI signals which require iterative calculations using complex equations, the calculation of the Sindex is direct and straightforward making the processing time extremely short and compatible with real-time processing (Sindex results being obtained while the patient is still installed in the MRI scanner, providing opportunities to carry additional scanning depending on the results).

Furthermore, this approach based on IVIM/diffusion MRI has the potential to give a semi-automatic diagnosis of lesions with high accuracy without the need for contrast agents, an important benefit for patients exposed to the risk of Nephrogenic Systemic Fibrosis (NSF). This approach has great potential for the diagnosis of breast, prostate, head and neck, pancreas and lung cancer lesions.

According to a fourth application of the method, an identification of blood vessels in tissues can be performed and is based on their "signature", as a signal decay higher than 90% due to the IVIM effect between b=0 and b=100 s/mm² IVIM/diffusion MRI signals. As for the first and second applications of the method 42, an IVIM/Kurtosis model may be used. But, as in this case, the high key b value is only Hb=100 s/mm2 while the low key b value is set at Lb=0. Here, a voxel with a very high sADC, for instance larger than $3*10^{-3}$ mm²/s, is flagged as containing a large blood vessel. One may also use the normalized or the scaled normalized signature index by considering a voxel containing a large blood vessel as a first pole reference tissue and a voxel without a large blood vessel as a second pole reference tissue. Regardless of the kind of signature index used, the voxels containing such vessels can then be flagged and removed from the lesion for a more accurate tissue analysis (using the signature index method or any other analysis method, for instance with the fitting of parameters of an IVIM/non-Gaussian diffusion model), or used to generate 3D IVIM angiograms as shown in the 3D IVIM angiogram of FIG. 11. This example of angiogram obtained in a normal human breast tissue shows blood vessels 152 darker than the normal tissue. The invention has the potential to generate angiograms with high accuracy without the need for contrast agents, an important benefit for patients exposed to the risk of Nephrogenic Systemic Fibrosis (NSF).

Another field of application of the signature index Sin or SI is Magnetic Resonance (MR) Elastography.

As described by the document U.S. Pat. No. 5,899,858 A (Ref. #12), the conventional approach relies on the phase shift of the MRI signal induced by mechanical vibrations.

Mechanical vibrations are firstly induced in the observed tissue by using an external driver at a predetermined frequency generally comprised in an interval ranging from 25 Hz to 500 Hz. Those vibrations induce shear waves in tissues which propagate at a speed depending on the tissue elasticity properties (Young modulus, shear stiffness). In turns, the shear waves induce a phase shift of the MRI signal when occurring in the presence of motion-probing gradient pulses, similar to those used for IVIM and diffusion MRI, and oscillating at the same frequency than the mechanical vibrations.

Then, two measurements are acquired by alternating the polarity of the motion-probing gradients and the resulting phase images are subtracted to produce a phase shift map reflecting the propagating mechanical wave in the tissue. By repeating the measurements over several cycles (typically 8 cycles) the spatial wavelength λ of the propagating waves can be estimated. The shear modulus μ can then be calculated and imaged voxel-by-voxel on the basis of the following relationship:

$$\mu = \rho \cdot (f\lambda)^2 \qquad \text{equation \#13}$$

where f is the vibration frequency and the tissue density that is around kg/l.

Such a conventional approach suffers from several drawbacks, notably long acquisition times as several waves have to be recorded, a limited spatial resolution to accommodate long waves lengths, synchronization difficulties when acquiring multiple slices of 3 datasets, complex and time consuming reconstruction algorithms, in particular for phase unwrapP1ng images.

Figure 12:
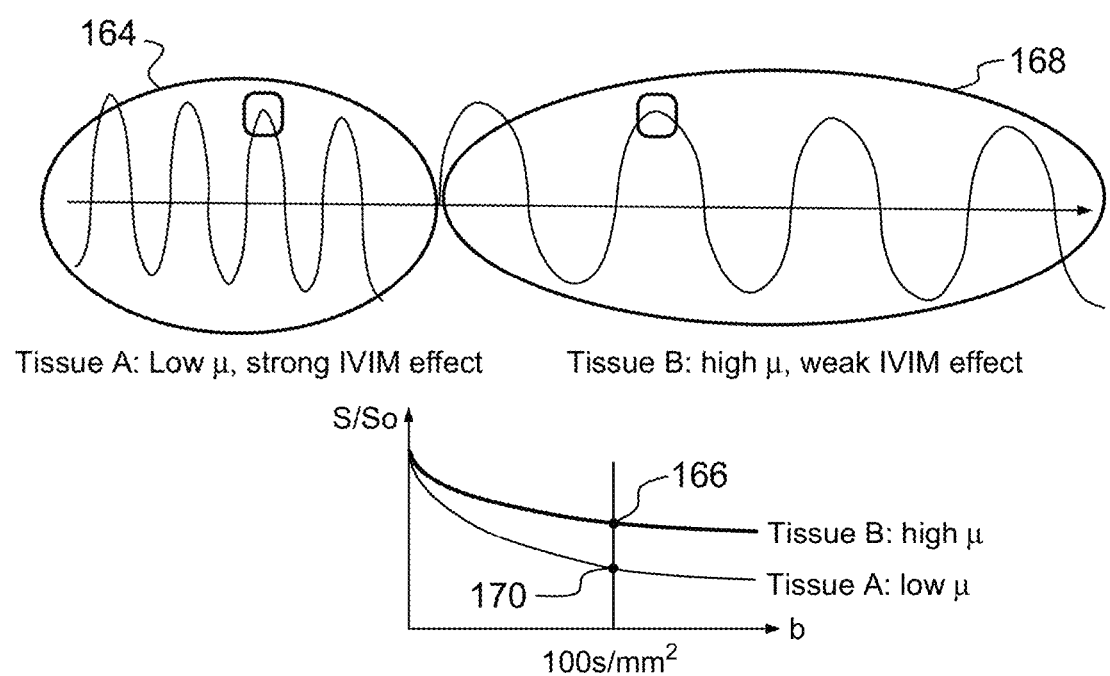
FIG. 12 is a set of three views illustrating the underlying principle of the IVIM elastography method.

As illustrated in FIG. 12, the basic approach of the MRE method according the invention, designated as IVIM MRE method, is to consider that in the presence of motion-probing gradient pulses vibration or shear wave induced phase dispersion within each voxel is responsible for a decrease of the signal amplitude, similar to the IVIM effect. Spatially sharp waves associated to a low shear modulus and shown in the spot 164 will generate a stronger MR signal attenuation 166 (considered at b=100 s/mm²) than spatially smoothed waves associated to a high shear modulus and shown in the Figure spot 168 (showing lower signal attenuation 170 at b=100 s/mm²), so that a contrast will be "naturally" generated in the magnitude image without the need for any specific processing.

The vibration induced signal amplitude attenuation S(b)/So in a given voxel, at location [r, r+p] where p is the pixel size, for a b-value, b, can be calculated as:

$$S(b)/So = \int_r^{r+p} dr \exp[i(\varepsilon/\pi)\sqrt{48bNf}\sin(r/\lambda+\theta)] \qquad \text{equation \#14}$$

where f is the vibration frequency, ε is the amplitude of the vibration, θ the phase offset of the vibration, λ is the spatial wavelength and N the number of periods of the motion-probing gradients.

By using the relationship between the shear modulus μ and the spatial wavelength λ expressed by the equation #13, the spatial wavelength λ can be replaced in the equation #14 by the expression:

$$\lambda = 1/f\sqrt{K \cdot \mu/\rho} \qquad \text{equation \#15}$$

The degree of attenuation will depend on the tissue elasticity and on the acquisition parameters (mainly b value, pixel size, vibration frequency and amplitude).

Considering that tumors or lesions generally have large shear modulus than normal tissues one may find a suitable frequency range for the vibration which will cancel the signal in the normal tissue while only slightly reducing the lesion signal, making lesions highly visible, based on their shear stiffness.

It should be noted that this "magnitude" effect has been described earlier in the article from Glaser K. J. et al. entitled "Shear Stiffness Estimation Using Intravoxel Phase Dispersion in Magnetic Resonance Elastography", published in Magnetic Resonance in Medicine, 2003, 50:1256-1265 (Ref.#13), or in the document U.S. Pat. No. 5,825,186 A (Ref.#14), but the "phase" approach remains so far the standard method.

One reason why the "amplitude" based method has not been used in practice is that it may be difficult to quantitatively retrieve the elasticity modulus μ from the signal attenuation by inverting the equation #14. Furthermore, the method described in those two references does not take into account concomitants IVIM and diffusion effects, which also lead to a MR signal attenuation and are a possible source of errors in the determination of elasticity.

Figure 13:
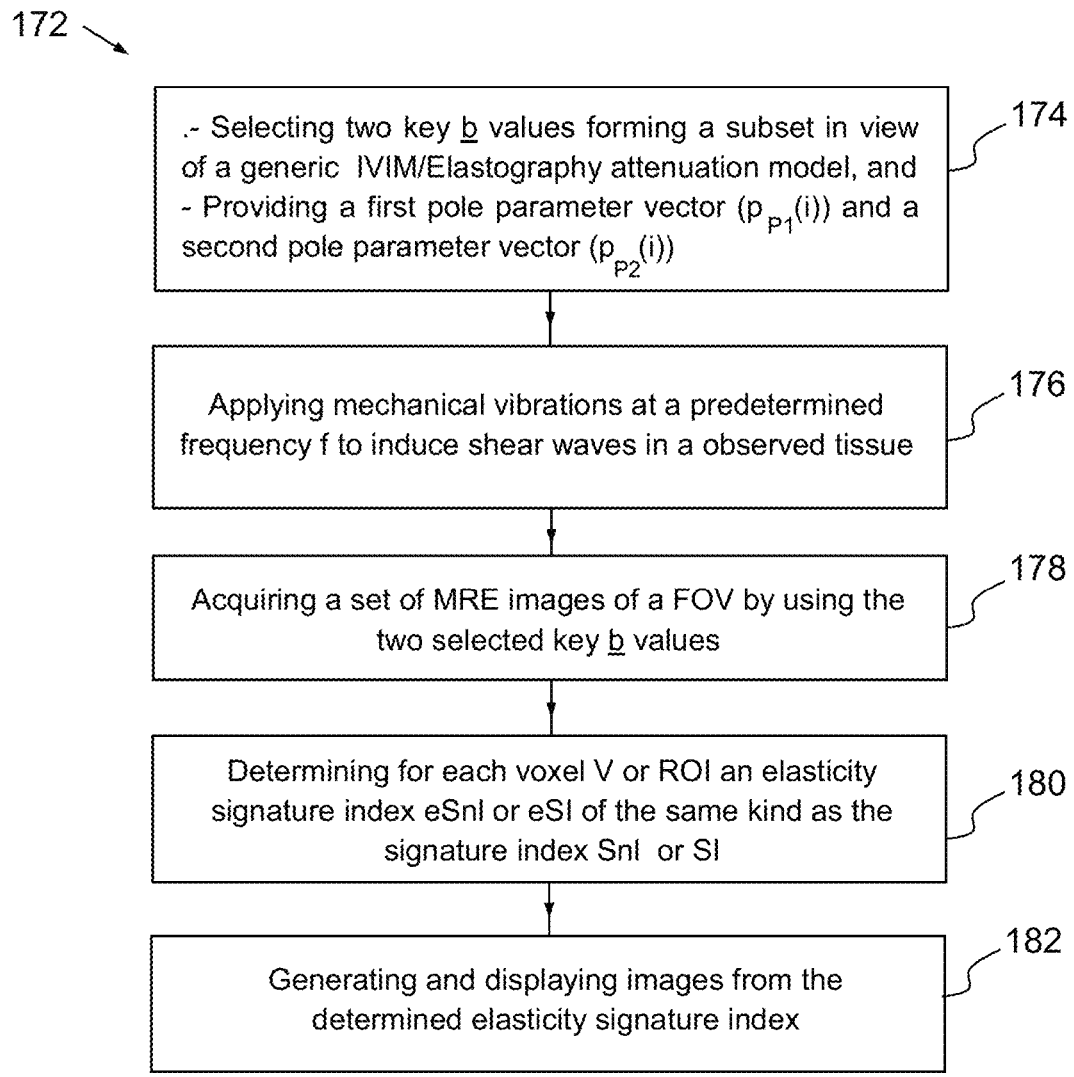
FIG. 13 is a flow chart of an IVIM elastography method for generating real IVIM elastograms by using the method of FIG. 3 and an external driver.

According to FIG. 13, the IVIM Magnetic Resonance Elastography method 172 consists in obtaining images and measurements in ROIs or voxels of tissue elasticity or shear stiffness, by executing a set of first, second, third, fourth and fifth steps 174, 176, 178, 180 and 182.

In the first step 174, two key b values are selected on the basis of this IVIM/Elastography effect using equation #14 as a generic IVIM/elastography attenuation model combined if necessary, with equation #10.

The IVIM/elastography effect and the IVIM/Non Gaussian effects are independent and the total signal attenuation is the product of their attenuation effects. The high key b value is for instance around Hb=100 s/mm² while the lower key b value is set at Lb=0. With such a low Hb value IVIM and diffusion effects are usually negligible with respect to the IVIM/Elastography effect the equation #14 alone can represent an acceptable generic signal attenuation function.

In the first step 174 and in order to prepare the calculation of an elasticity signature index eSI, a first pole reference model parameter vector ($p_{P1}(i)$) and a second pole reference parameter vector ($p_{P2}(i)$) that correspond respectively to a first actual state P1 and a second actual state P2 are provided. The first actual state P1 is the microstructure state of a first reference tissue having a predetermined high stiffness while the second actual state P2 is the microstructure state of a second reference tissue having a predetermined low high stiffness. The first pole reference model parameter vector ($p_{P1}(i)$) and the second pole reference parameter vector ($p_{P2}(i)$) being previously identified once for all during a preliminary calibration process carried with induced shear waves at the predetermined shear waves frequency before executing the method 172. An advantage of the signature method is that the elasticity signature index will intrinsically take into account IVIM and diffusion effects.

However, in a particular case where Hb is low enough so that IVIM and diffusion effects can be neglected and the parameter vector is reduced to the elasticity parameters, such as the elasticity modulus μ at a given frequency or a set of values representing elasticity at different vibration frequencies.

Then, in the second step 176 mechanical vibrations are induced in the observed tissue by using an external driver at a predetermined frequency generally comprised in an interval ranging from 25 Hz to 500 Hz. Those vibrations induce shear waves in tissues which propagate at a speed depending on the tissue elasticity properties (Young modulus, shear stiffness). In turns, the shear waves induce a phase shift of the MRI signal when occurring in the presence of motion-probing gradient pulses, similar to those used for IVIM and diffusion MRI, and oscillating at the same frequency than the mechanical vibrations.

Then, while the second step 176 is still being carried out, in the third step 178 a set of modulus MR Images of a Field of View (FOV) of the tissue is acquired by using a motion-probing pulse gradient MRI sequence configured at the two key b values.

Then in the fourth step 180, on a one-per-one voxel basis or on a predetermined Region Of Interest (ROI) including a set of voxels, an elasticity signature index eSnl of the ROI/voxel at the predetermined frequency is determined, in the same way as performed for the determining the normalized index Snl concerning the degree of malignancy of human breast tumor tissue or the degree of malignancy of rat brain tumor tissue, by using equation #14 combined with equation #10 to determine the pole reference model signal patterns at one or several vibration frequencies and the corresponding values for Sdist1 and Sdist2. From the normalized index eSnl, a scaled signature index eSI can be derived using a linear or non linear calibration transformation. In this case the absolute scale represents the degree of shear stiffness or the elasticity modulus, although the elasticity modulus has not been formally calculated from the images.

For instance, if the shear modulus of the first pole state P1 is 75000 Pa and the shear modulus of the second pole state P2 is 25000 Pa, assuming in first rough approximation a linear dependency of the signature index with the shear modulus one may define an elasticity signature index eSI as:

$$eSI=(eSnl+1)*25000+25000 \qquad \text{equation \#16}$$

In the optional fifth step 182, images are generated by using the determined signature eSI on a voxel-by-voxel basis and displayed.

In a further improvement of the method 172, two sets of images are acquired with phase offset θ separated by π/2 can be averaged before calculating the elasticity index eSI. This step will reduce the so called "venetian blind" effect which can be sometimes observed in IVIM/Elastograms as the signal amplitude in the image is modulated in space along the direction of the propagating wave with a period of by π/2.

In the IVIM MRE method 172, a signature index reflecting elasticity of a tissue in a voxel V is obtained without the need for calculating its elasticity modulus.

Conversely to the phase shift conventional MR elastography method as described in the document U.S. Pat. No. 5,899,858, the IVIM MR elastography method 172 according to the invention avoids several drawbacks, notably long acquisition times since several wave cycles have to be recorded, a limited spatial resolution to accommodate long wave lengths, synchronization difficulties when acquiring multiple slices or three datasets, complex and time-consuming reconstruction algorithms in particular for phase unwrapP1*ng* across the images.

Figure 14:
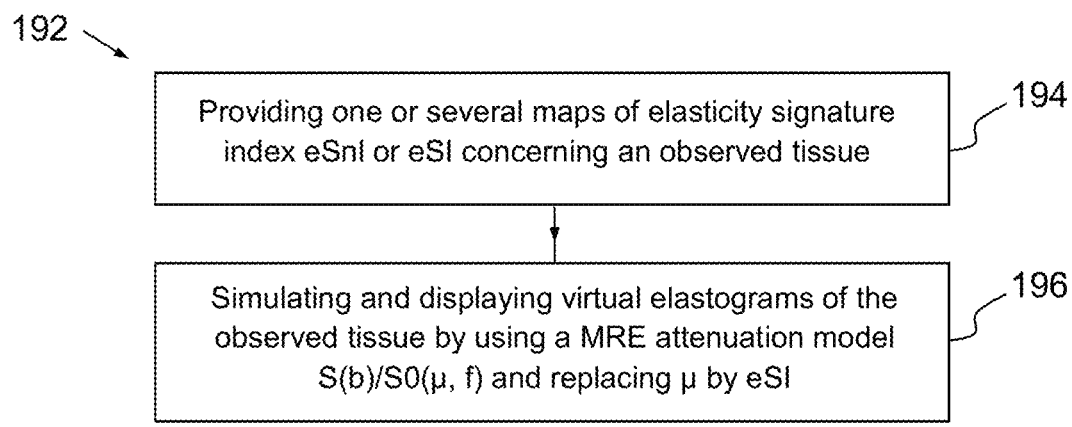
FIG. 14 is a flow chart of an IVIM elastography method for emulating virtual IVIM elastograms by using the method of FIG. 3.

According to FIG. 14, a Magnetic Resonance Elastography emulation method 192 for generating virtual elastograms is illustrated.

Assuming that the elasticity signature index reflects the shear elasticity modulus μ, virtual IVIM/elastogram images can be produced for any combination of acquisition parameters (mainly b value, pixel size, vibration frequency and amplitude) using equation #14 to calculate maps where contrast is based on the $S(b)/S_0$ attenuation. The virtual signal attenuation for each voxel is calculated from the equation #14 and equation #15 using for the shear elasticity modulus μ the elasticity signature index. The emulation method allows virtual elastogram images to be obtained without the need to acquire additional real data. For instance this method will dramatically cut in acquisition times as virtual elasticity images can be produced for any vibration frequency using data acquired at a given frequency. Emulation method 192 also allows to generate virtual elastogram images for acquisition parameters beyond technically available values for instance regarding magnetic field gradient strength required for some pixel sizes or vibration frequencies, or for vibration amplitudes which cannot been reached because of mechanical limitations (for instance because the tissue is located too deeply within the body).

Generally, the Magnetic Resonance Elastography emulation method 192 for generating virtual elastograms comprises a first step 194 and a second step 196. In the first step 194, one or several maps of elasticity signature index concerning an observed tissue are provided. Then, in the second step 196, by using an MRE attenuation model wherein the attenuated signal depends of the shear stiffness and the frequency, and by replacing the mapped shear stiffness by the mapped elasticity index in the MRE attenuation model, elastograms of the observed tissue are simulated and displayed at different vibration frequency and/or amplitude. These images have a contrast driven by tissue shear stiffness properties.

This capacity to generate virtual elastograms can even be further extended to cases where external vibrations cannot be used at all. It should be noted that some link is expected between tissue elasticity and tissue water diffusion properties as described in the article from Alkalay R. N. et al., entitled "MR Diffusion is Sensitive to Mechanical Loading in Human Intervetebral Disk Ex Vivo", JMRM2015, 41:654-664 (Ref.#15), wherein some link is expected between tissue elasticity and tissue water diffusion properties.

As non-Gaussian diffusion closely relates tissue microstructure one may consider that a signature index SI, or even a signature index sADC, is closely related to the shear modulus μ. Using only data acquired at the key b values the normalized signature index Snl obtained with method 42 (i.e. without using any mechanical vibration) can be converted into a pseudo-elasticity signature index according to a predetermined transformation function g(·) linking the normalized signature index Snl and the shear stiffness μ as μ=g(Snl) equation #17, or according to a predetermined transformation function h(·) linking the signature index sADC and the shear stiffness μ as μ=h(sADC).

The predetermined transformation functions g(·) anf h(·) are monotonous functions and are preferably linear functions.

Figure 15:
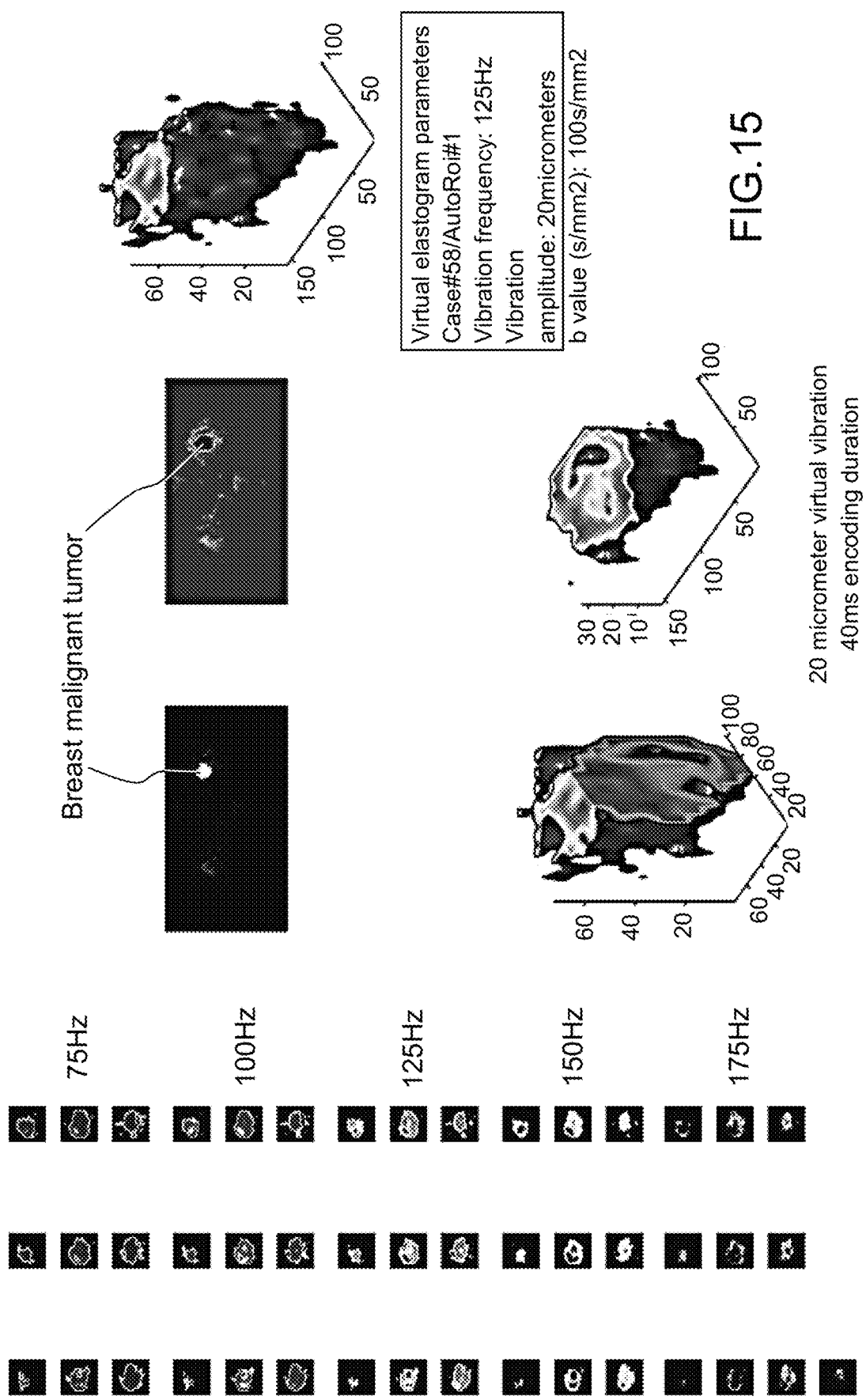
FIG. 15 is a set of virtual elastograms of a human breast tumor obtained with a set of Snl index cut images.

As illustrated in FIG. 15, a simulation of IVIM virtual elastograms has been successfully carried out by exploiting Snl maps of nine slices obtained from diffusion images acquired in a patient and extracted from the first article of lima M. et al.

For this demonstration a simple direct linear relationship, such as μ=K*eSI (equation #15), where K is a constant, has been assumed although other models are possible:

$$eSI=(Snl+1)*25000+25000 \qquad \text{equation \#18}$$

Within a suitable frequency range, voxels with high Snl will appear much brighter than voxels with a low Snl. At a very high frequency all voxels will have a very low signal while at very low frequency all voxels will have no signal attenuation. Indeed, the effect can be enhanced or decreased by adjusting the vibration frequency, the vibration amplitude, the b-value and even the (virtual) voxels size, creating new contrasts useful to highlight lesion heterogeneity.

Figure 16:
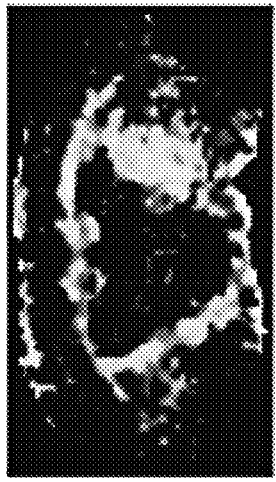
FIG. 16 is a set of virtual elastograms of a mouse brain tumor obtained with a signature index (Sindex) image.
Figure 16:
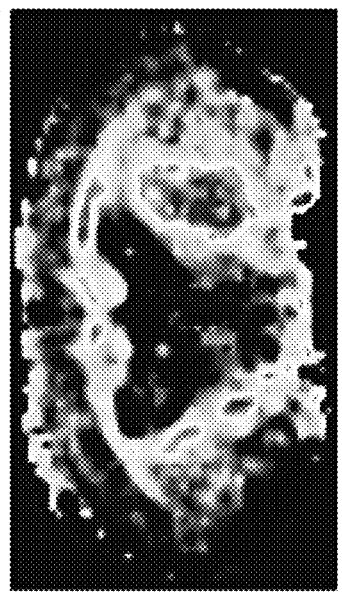
Figure 16:
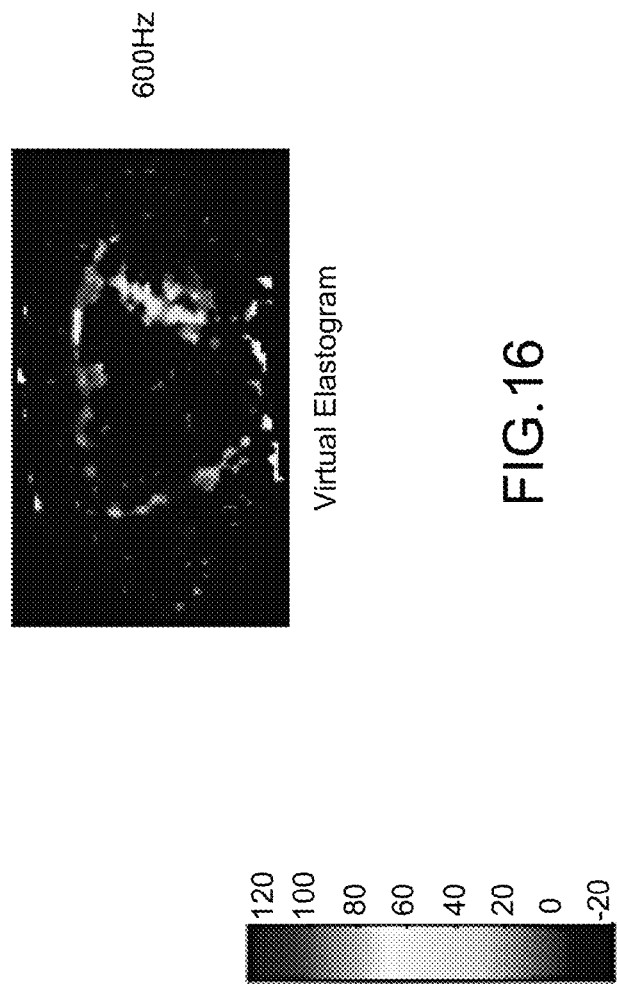

According to another example illustrated in FIG. 16, virtual elastograms were obtained in the brain of a mouse with an implemented glioma (collaboration with S. Mériaux, F. Geoffroy, E. Peres, NeuroSpin). Virtual elastograms at 600 HZ and 770 Hz show an internal track corresponding to the tumor infiltration not visible on conventional T2 or even diffusion MRI images, although the Sindex does not carry intrinsically more information than the diffusion images. The virtual elastogram, thus, appears as a filter revealing structure within the diffusion MRI images based on virtual elastic properties which will be otherwise not visible, even on classical elastograms since such high frequencies cannot be obtained with current devices.

Thus, from the Snl (or SI), it is possible to generate virtual MR elastograms reproducing the experimental conditions of MRE, both for the phase and amplitude approaches.

Figure 17:
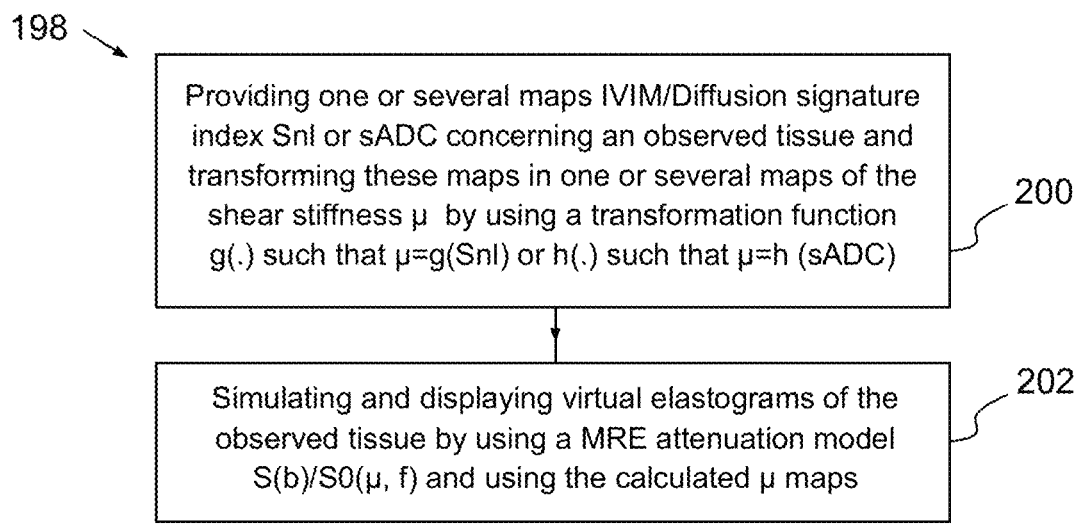

According to the FIG. 17, in such a variant 198 from the MRE emulation method 192 of FIG. 14, the first step 194 is replaced by a third step 200 and the second step 196 is replaced by a fourth step 202.

In the third step 200, one or several maps of the normalized signature index Snl or of the signature index sADC, obtained from IVIM/non-Gaussian framework are provided and translated into shear stiffness maps according to a predetermined transformation function g($\cdot$) linking the normalized signature index Snl and the shear stiffness $\mu$ as $\mu$=g(Snl) equation #17, or according to a predetermined transformation function h($\cdot$) linking the signature index sADC and the shear stiffness $\mu$ as $\mu$=h(sADC).

The predetermined transformation functions g($\cdot$) anf h($\cdot$) are monotonous functions and are preferably linear functions.

In the fourth step 202, virtual elastograms of the observed tissue are simulated and displayed at any given frequency f comprised in any interval ranging from 1 Hz to 10000 Hz by using a MRE attenuation model and using any combination of acquisition parameters (vibration frequency and amplitude, voxel size, MPG amplitude and duration), and by using the shear stiffness maps determined from the normalized signature index Snl or sADC maps.

Figure 18:
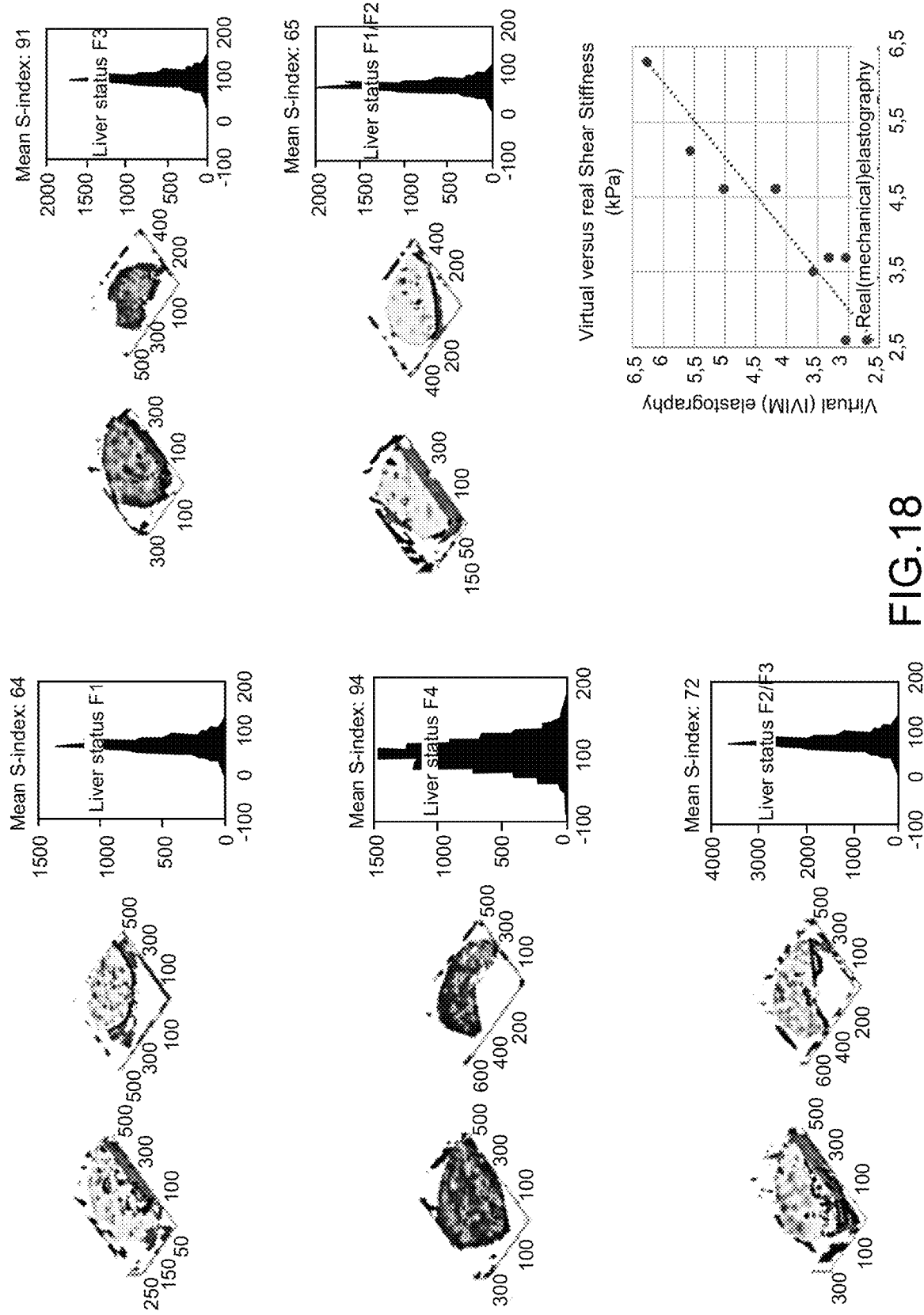
FIG. 18 is a set of Sindex images corresponding to different degrees of liver stenosis and closely reflecting the elastic properties as verified by conventional mechanic liver elastography.

As illustrated in the FIG. 18, preliminary results were obtained in a series of nine patients presenting different degrees of liver stenosis (unpublished results, collaboration with Pr. Ichikawa, Yamanashi University, Japan). Colored-scaled Sindex images closely reflect liver elastic properties as verified by conventional (mechanic) liver elastography. For instance, patients with high grade liver fibrosis (F4) have a Sindex around 90-95, corresponding to real shear stiffness around 5.5-6.5 kPa. On the other hand, patients with a low grade of liver fibrosis (F1-F2) had Sindex values around 65, corresponding to real shear stiffness around 2.5-3.5 kPa. Patients with intermediate stages (F3) with shear stiffness around 4.5 kPa had a Sindex around 70-75.

In this series of patients an even stronger linear relationship was found between sADC and $\mu$ with $\mu$ (kPa)=14.46-13274 sADC (mm$^2$/s). Hence, the liver shear stiffness estimated from the liver sADC obtained from step 6 in all patients was extremely close to the actual shear stiffness obtained from real (mechanical) MR elastography measurements as illustrated in FIG. 16.

Figure 19:
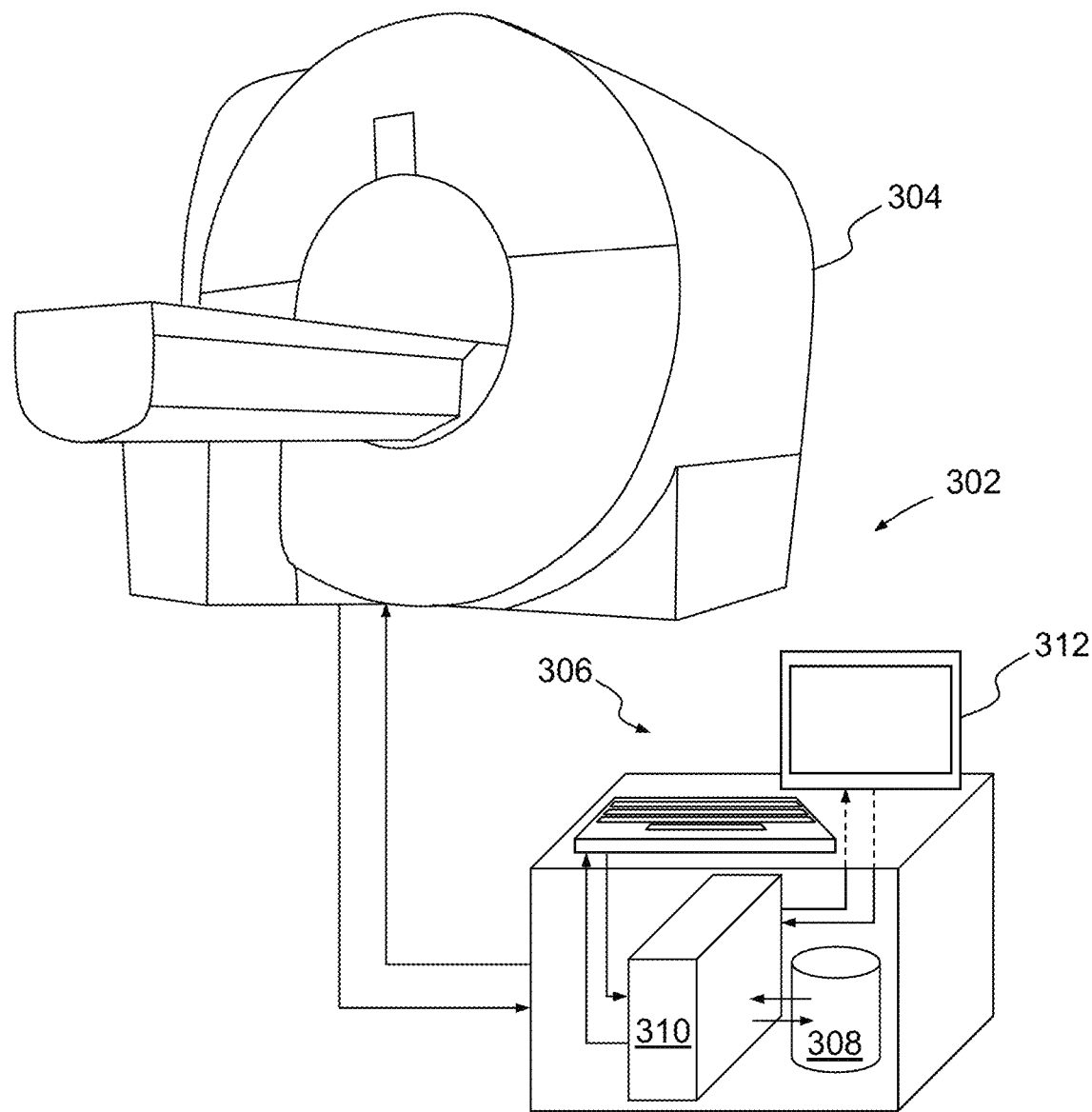
FIG. 19 is a view of an apparatus according to the invention for implementing the method as described in FIGS. 1, 3, 5, 13 and 14 and permitting the display of the signature index maps of FIGS. 10 to 11.

The advantages of such an approach (Virtual MR elastograms) are the following ones:
No need to use external mechanical vibrations, which allow also deep organs to be investigated No need for additional image acquisition, only the diffusion-sensitized images at key b values for the calculation of the SI are necessary, shear wave direction is identical to the direction of the gradient pulses used for diffusion encoding, Virtual Elastograms have the same features than the IVIM/diffusion (real) images in terms of spatial resolution and multi-slice/3D acquisition capabilities, Virtual MR elastograms based on signal amplitude attenuation intrinsically have a correction for IVIM/diffusion effects, No background phase effects and no need for phase reconstruction algorithms Virtual MR elastograms can be produced in real-time for any ranges of (virtual) vibration frequencies to get optimal contrast, and any range of gradient strength, potentially above the MRI scanner gradient hardware limits According to FIG. 19, an apparatus 302 for determining one or several signature indices of an observed tissue, representative sensitively of a type of tissue or representative of microstructure or biological state of a type of tissue, from motion-probing pulses gradient Magnetic Resonance Images (MRI) of the observed tissue comprises a magnetic resonance imaging scanner 304 to operate motion-probing pulses gradient Magnetic Resonance Imaging with a high resolution and accuracy and means 306 for controlling the scanner 304 and processing the imaging data acquired by the scanner 304.

The magnetic resonance imaging scanner 304 is configured for acquiring a set of MRI images of a Field Of View (FOV) of the observed biological issue by using a same motion-probing pulses gradient sequence, programmed with gradient configured to obtain the determined key $\underline{b}$ values of the subset.

The means 306 for controlling the scanner and processing the imaging data acquired by the scanner comprises storage means 308, processing means 310, and display means 312.

The storage means 308 are configured for storing:
a generic attenuation model of a diffusion MRI attenuated signal S(b), representative of the type of the tissue to be observed, suited to Intra Voxel Incoherent Motion (IVIM) and/or non-Gaussian signal patterns, and expressed by a model function f(b) depending on a gradient attenuation factor $\underline{b}$ and on a first set of NP model parameters p(i) characterizing the type of tissue and the microstructure state, the said model parameters p(i) defining a model parameter vector space; and
a reference model parameter vector ($p_R$(i)) corresponding to a neutral or an average state or a specific state of the tissue, defining through the generic attenuation model a neutral reference model diffusion MRI attenuated signal $S_R$(b).

The reference model parameter vector ($p_R$(i)) corresponds generally to a reference state of the tissue.

The processing means 310 are configured for:
for each model parameter p(i), determining a key b value that maximizes a partial differential sensitivity $dS_i$(b) of the generic model diffusion MRI attenuated signal S(b) to the said model parameter p(i) at the neutral reference model diffusion MRI attenuated signal $S_R$(b) over a predetermined interval of $\underline{b}$ values ranging from zero to a predetermined maximum value $b_{max}$;
determining from the NP key b values a key b value subset by removing the key $\underline{b}$ values that are associated to model parameters of low interest for tissue type and/or the microstructure or biological state to characterize; and on a one-per-one voxel basis or on a predetermined Region Of Interest (ROI) including a set of voxels, determining a signature index (sADC(V), Sdist(V), Snl(V), SI(V)) of the voxel V as a real number representative of the microstructure state and the type of the tissue present in the ROI or the voxel V, the signature index being a scalar function depending on the voxels signals acquired at the key b values of the key b value subset.

It should be noted that the scalar function defining the signature index depends directly on the voxel signals acquired at the key b value subset and does not use any generic attenuation model for the observed tissue.

A computer software comprises a set of instructions that, after being loaded in the means 306 for controlling the scanner and process the data, are executed to carry out partially or fully the steps as described in FIG. 1, FIG. 3, FIG. 4, FIG. 12 and FIG. 14.

It should be noted that the steps for processing the MRI data can be carried out on a standalone console different from the MRI scanner console through a dedicated computer software.

This new approach allows a dramatic cut on acquisition and processing times. Conversely to current approaches based on full fitting of MRI signals which require iterative calculations using complex equations, the calculation of the Sindex is direct and straightforward making the processing time extremely short and compatible with real-time processing. Real-time processing is understood as a processing that provides the results while the patient is still installed in the imaging device and that provides opportunities to carry additional scanning depending on the results previously obtained.

In the field of IVIM/Diffusion MRI the possible applications of the method for classifying tissues types according to invention and as described here above are as follows:

Automatic recognition of malignant/benign lesions;
Calculation of a Malignant charge index, i.e a lesion volume with malignant SI, which is useful to follow treatment efficacy;
Assessment of lesion heterogeneity based on SI histogram analysis, which permits to assess treatment efficacy which often increases homogeneity before decreasing tumor volume;
Differentiation of lesion types as for example cyst, angioma, tissue;
IVIM angiography: Recognition of vessels, with the possibility to produce angiograms without using contrast agents that have some risks;
IVIM elastography: Emulation of Magnetic Resonance elastography (image contrast based on tissue shear);
IVIM elastography: Generation of real IVIM MRE elastograms by using SI maps derived from modulus IVIM MRE images.

For other MRI modalities, the possible applications of the method of the invention is Contrast Enhanced MRI by recognition of malignant/benign lesions and differentiation of tissue types based on contrast uptake signatures;

As regards the improvement in data processing of classical approaches through the image processing algorithms, the method according to the invention improves:

3D clustering to eliminate/correct voxels with spurious (noisy) signal values

Automatic detection and delineation of lesions based on SI thresholds before conducting more standard analyses Fast display of lesion slices and 3D rendering, including 3D movies showing lesion features.

The invention claimed is:

1. A method for determining one or several signature indices of an observed tissue, representative sensitively of a type of tissue or representative sensitively of a microstructure or biological state of a type of tissue, the signature indices being determined from motion-probing pulses gradient Magnetic Resonance Images (MRI) of the observed tissue, and the method comprising the steps of:

providing a generic attenuation model of a diffusion MRI attenuated signal S(b), representative of the type of the tissue to be observed, suited to Intra Voxel Incoherent Motion (IVIM) and/or non-Gaussian signal patterns, and expressed by a model function f(b), depending on a gradient attenuation factor b and on a first set of model parameters p(i) characterizing when valued the type of tissue and the microstructure state, said model parameters p(i) defining a model parameter vector space and NP being a number of model parameters of the first set;

providing a reference model parameter vector $(p_R(i))$ corresponding to a reference state of the tissue, defining through the generic attenuation model a generic reference diffusion MRI attenuated signal $S_R(b)$; then thereafter for each model parameter p(i), determining with an image data processing device, a key b value that maximizes a partial differential sensitivity $dS_i(b)$ of the generic model diffusion MRI attenuated signal S(b) to the said model parameter p(i) at the reference model parameter vector $(p_R(i))$ over a predetermined interval of b values ranging from zero to a predetermined maximum value $b_{max}$; then thereafter determining with the image data processing device from the NP the key b values previously determined, a key b value subset by removing the key b values that are associated to model parameters of low interest for tissue type and/or the microstructure or biological state to characterize; then thereafter acquiring with the image data processing device a set of MRI images of a Field Of View (FOV) of the observed tissue by means of a motion-probing pulsed Gradient MRI sequence programmed with gradient configured to obtain the determined subset of key b values; then thereafter on a one-per-one voxel basis or on a predetermined Region Of Interest (ROI) including a set of voxels, determining with the image data processing device the signature indices that include a signature index of the voxel V or the ROI as a real number representative of the microstructure state and the type of the tissue present in the ROI or the voxel V, wherein the signature index being a scalar function depending directly on the voxel signals acquired at the key b values of the key b value subset, without using any generic attenuation model for the observed tissue.

2. The method for determining one or several signature indices of an observed tissue according to claim 1, wherein during the determining of the key b values subset, a further filtering is carried out by removing the key b values that provide the MRI signal with a sensitivity $dS_i(b)$ to the model parameters p(i) around the reference signal $S_R(b)$ below a predetermined sensitivity threshold and/or that higher than the validity range of the used generic attenuation model and/or which may results in values below a predetermined noise threshold level.

3. The method for determining one or several signature indices of an observed tissue according to claim 1, wherein:

the key b values subset has a cardinality equal to 2 and includes a low key b value Lb and a high key b value Hb, and the signature index of a voxel is a signature index of a first kind, designated as a synthetic ADC (sADC) including Intra Voxel Incoherent Motion (IVIM) Gaussian and non-Gaussian components present in the voxel signals, and calculated according to the expression:

$$sADC(V) = Ln[S_V(Lb)/S_V(Hb)]/(Hb-Lb),$$

where $S_V(Lb)$ designates the measured signal of the voxel for the MRI image acquired with the key b=Lb, and $S_V(Hb)$ designates the measured signal of the voxel for the MRI image acquired with the key b=Hb.

4. The method for determining one or several signature indices of an observed tissue according to claim 1, wherein:

the signature index is a signature index of a second kind, designated as Sdist, that is determined by calculating a pseudo-distance between the vector signal pattern observed at the key b values $b_k$ in the ROI or voxel $S_V(b_k)$ and the vector signal pattern calculated in the reference state tissue R using the generic attenuation model $S_R(b_k)$, k designating an integer rank of the key values running over the key b values subset; and the pseudo-distance is an algebraic distance or a correlation coefficient or a scalar product between $S_V(b_k)$ and $S_R(b_k)$ or any kind of distance.

5. The method for determining one or several signature indices of an observed tissue according to claim 4, wherein:

the signature index of second kind Sdist is calculated by the expression:

$$Sdist(V) = \sum_{b_k \in key\ b\ values} (-1)^{G(b_k)}[S_V(b_k) - S_R(b_k)]/S_R(b_k),$$

and where $G(b_k)$ is an integer that can be even or odd depending on the sign of $dS(b_k)$ with $dS(b_k)=[S_V(b_k)-S_R(b_k)]/S_R(b_k)$.

6. The method for determining one or several signature indices of an observed tissue according to claim 1, wherein the signature index is an extension of a signature index of a second kind, designated by SCdist, that is determined by calculating a pseudo-distance between an 2D-array signal pattern $S_V(b_{k(m)}, Cm)$ observed at different key b values $b_{k(m)}$ under different conditions Cm in the ROI or voxel and the 2-D-array signal pattern $S_R(b_{k\ (m)}, Cm)$, calculated in a reference state tissue R using a generic attenuation model, where m designates an index identifying the MPG condition in a set of MPG conditions ranging from 1 to a integer number c, and k(m) designates the integer rank of the key b values of the subset corresponding to the condition Cm, and the pseudo-distance is an algebraic distance or a correlation coefficient or a scalar product between $S_V(b_{k(m)}, Cm)$ and $S_R(b_{k(m)}, Cm)$ or any kind of distance, a particular distance being defined as:

$$SCdist(V; R) = \sum_{m=1\ to\ c;\ b_k(m) \in key\ b\ values} (-1)^{G(b_k(m),Cm)}[S_V(b_k(m), Cm) - S_R(b_k(m), Cm)]/S_R(b_k(m), Cm)$$

where $G(b_{k(m)}, Cm)$ is an integer that can be even or odd depending on the sign of $[S_V(b_k(m), Cm)-S_R(b_k(m), Cm)]/S_R(b_k(m), Cm)$; and particular conditions Cm being different orientations in space of the MPG pulses to take into account diffusion anisotropy and/or different diffusion times, defined by the time interval and the duration of the MPG, to take into account restricted diffusion effects.

7. The method for determining one or several signature indices of an observed tissue according to claim 5, comprising the steps of:

calculating a number r of signature distances, Sdist(V; $R_j$) or SCdist(V; $R_j$), between the observed tissue and different predetermined reference tissues Rj, wherein j is an integer index identifying the reference tissue Rj and is ranging from 1 to r, and wherein Sdist(V; $R_j$) and SCdist(V; $R_j$) are respectively defined according to claim 5; then identifying the tissue state or type of the observed tissue as that of the reference tissue $R_{j0}$, where the reference tissue index $j_0$ is such that:

$$Sdis(V;Rj_0) = Min_{j=1\ to\ r}(Sdist(V;R_j))$$

or $$SCdist(V;Rj_0) = Min_{j=1\ to\ r}(SCdist(V;R_j)).$$

8. The method for determining one or several signature indices of an observed tissue according to claim 1, comprising further between the first step and the second step a seventh step of:

providing a first pole reference model parameter vector ($p_{P1}(i)$) and a second pole reference parameter vector ($p_{P2}(i)$), corresponding each one to a first calibrating state P1 and a second calibrating state P2 of the same type of tissue as the observed tissue, and calculated from preliminary MRI images acquired in a preliminary step of calibration, or from previously established values, the first and second calibrating states P1, P2, as well their corresponding reference model parameter vectors ($p_{P1}(i)$),($p_{P2}(i)$), being different.

9. The method for determining one or several signature indices of an observed tissue according to claim 8, wherein the second step is replaced by an eight step of:

calculating a neutral reference model parameter vector $p_N(i)$ as the average sum of the first pole reference model parameter vector ($p_{P1}(i)$) and the second pole reference parameter vector ($p_{P2}(i)$).

10. The method for determining one or several signature indices of an observed tissue according to claim 8, wherein the first calibrating state P1 of the tissue to the second calibrating state P2 correspond to:

a "benign" versus "malign" tissue for a tumor tissue, or a tissue under medical treatment versus an untreated tissue, or a "resting" versus an "activated" tissue, or a "normal" versus an "inflammatory" tissue, or a tissue with a "first spatial orientation" versus a tissue with a "second spatial orientation" for an anisotropic tissue as in muscles, the heart or brain white matter tissue, or a tissue with a "first kind of cytoarchitectony" versus a tissue with "a second kind of architectony" for a brain cortex tissue.

11. The method for determining one or several signature indices of an observed tissue according to claim 8, wherein the signature index is a normalized signature index of a third kind, designated as Snl, that uses a signature index of a second kind Sdist and is determined by using the expression:

$$Snl(V)=\{max([Sdist(V)/Sdist1],0)-[max([Sdist(V)/Sdist2],0)\}$$

where Sdist(V) is the second kind signature index of the voxel of the tissue under investigation, Sdist1 is the second kind signature index of the voxel of the first calibrating state P1, and Sdist2 is the second kind signature index of the voxel of the second calibrating state P2.

12. The method for determining one or several signature indices of an observed tissue according to claim 11, wherein the signature index is an absolute signature SI determined by scaling the normalized signature index Snl with a strictly monotonous function.

13. The method for determining one or several signature indices of an observed tissue according to claim 12, wherein:
ROI level statistics on absolute signature SI are determined such as mean, standard deviation, skewness or kurtosis for lesion heterogeneity, or malignant charge volume defined as the product of the voxel size and the number of voxels with a SI index above a predetermined malignant threshold; and/or
histograms are determined; and/or
images of absolute signature index SI are displayed using a color scale and shown with 3D rendering.

14. The method for determining one or several signature indices of an observed tissue according to claim 1, wherein:
the type of tissue is a tissue of the organs consisting of the brain, head and neck organs, breast, prostate, liver, pancreas, lung, heart, muscle or joints; and/or
the generic attenuation model used for the reference diffusion MRI attenuated signal is comprised in the set of models consisting of the polynomial or Kurtosis model, the bi-exponential model, the statistical model and the stretched model.

15. The method for determining one or several signature indices of an observed tissue according to claim 1, wherein the generic attenuation model is the IVIM/Kurtosis model and its model function S(b) is expressed as:

$$S(b)=[S_0^2\{f_{IVIM}\exp(-b\cdot D^*)+(1-f_{IVIM})\exp[-b\cdot ADC_0+(b\cdot ADC_0)^2 K/6]\}^2+NCF]^{1/2}$$

where $S_0$ is the signal acquired with no diffusion weighting for b equal to zero, $f_{IVIM}$ is the volume fraction of incoherently flowing blood in the tissue, D* is the pseudo-diffusion coefficient associated to the IVIM effect, $ADC_0$ is the virtual Apparent Diffusion Coefficient which would be obtained when b approaches 0, K is the kurtosis parameter K, and NCF is the Noise Correction Factor.

16. The method for determining one or several signature indices of an observed tissue according to claim 15, wherein the subset of key b values has a cardinality equal to 2 and includes a low key b value Lb and a higher key b value Hb, and a normalized signature index Snl of a voxel, designated by Snl(V) is calculated according to the expression:

$$Snl(V) = \left\{ \begin{array}{l} \max([dS_V(Hb)-dS_V(Lb)]/[dS_{P1}(Hb)-dS_{P1}(Lb)], 0) \\ -[\max([dS_V(Hb)-dS_V(Lb)]/[dS_{P2}(Hb)-dS_{P2}(Lb)], 0) \end{array} \right\}$$

With $$dS_X(b)=[S_X(b)-S_N(b)]/S_N(b)$$

For X=V, P1, P2 and for b=Hb, Lb, $S_{P1}(b)$, $S_{P2}(b)$, $S_N(b)$ being the signals corresponding respectively to a first actual state P1, a second actual state P2, and a neutral state previously identified by the model and their respective first pole reference model parameter vector $(p_{ref(Q1)}(i))$, second pole reference parameter vector $(p_{ref(Q2)}(i))$, and neutral reference model parameter vector $(p_N(i))$ so that the signals values $S_{P1}(Lb)$, $S_{P2}(Lb)$, $S_N(Lb)$, $S_{P1}(Hb)$, $S_{P2}(Hb)$, $S_N(Hb)$ can be calculated, and where $S_V(Lb)$ designates the measured signal of the voxel for the MRI image acquired with the lower key b value Lb, and $S_V(Hb)$ designates the measured signal of the voxel for the MRI image acquired with the higher key b value Hb.

17. The method for determining one or several signature indices of an observed tissue according to claim 1, comprising further a step of displaying at least one map of at least one signature index of the voxels belonging to the Region Of Interest.

18. An IVIM angiography method for recognizing blood vessels from an observed tissue comprising the steps of:
determining one or several maps of at least one signature index of the voxels of the observed tissue by using a method as claimed in claim 1, and an IVIM/non-Gaussian model generic attenuation signal model, wherein either a first low key b value Lb equal to zero and a high key b value Hb for which the signal decay due to the IVIM effect in a voxel containing only blood is above a predetermined threshold are selected, and a signature index sADC is determined, wherein the key b values subset has a cardinality equal to 2 and includes a low key b value Lb and a high key b value Hb, and the signature index of a voxel is a signature index of a first kind, designated as a synthetic ADC (sADC) including Intra Voxel Incoherent Motion (IVIM) Gaussian and non-Gaussian components present in the voxel signals, and calculated according to the expression:

$$sADC(V)=\mathrm{Ln}[S_V(Lb)/S_V(Hb)](Hb-Lb)$$

where $S_V(Lb)$ designates the measured signal of the voxel for the MRI image acquired with the key b=Lb, and $S_V(Hb)$ designates the measured signal of the voxel for the MRI image acquired with the key b=Hb, or a voxel containing a large blood vessel is considered as a first pole reference tissue and a voxel without a large blood vessel is considered as a second pole reference tissue, and a normalized signature index Snl is determined, comprising further between the first step and the second step, a seventh step of:

providing a first pole reference model parameter vector ($p_{P1}(i)$) and a second pole reference parameter vector ($p_{P2}(i)$), corresponding each one to a first calibrating state P1 and a second calibrating state P2 of the same type of tissue as the observed tissue, and calculated from preliminary MRI images acquired in a preliminary step of calibration, or from previously established values, the first and second calibrating states P1, P2, as well their corresponding reference model parameter vectors ($p_{P1}(i)$),($p_{P2}(i)$), being different, wherein the signature index is a normalized signature index of a third kind, designated as Snl, that uses a signature index of a second kind Sdist and is determined by using the expression:

$$Snl(V)=\{max([Sdist(V)/Sdist1],0)-[max([Sdist(V)/Sdist2],0)]\}$$

where Sdist(V) is the second kind signature index of the voxel of the tissue under investigation, Sdist1 is the second kind signature index of the voxel of the first calibrating state P1, and Sdist2 is the second kind signature index of the voxel of the second calibrating state P2, and deriving and displaying angiograms from the at least one signature index maps.

19. An IVIM Magnetic Resonance Elastography method for determining IVIM elastograms and/or a shear stiffness based image contrast of an observed tissue comprising the steps of:

selecting two key b values in view of a generic IVIM/elastography attenuation model by providing a generic attenuation model of a diffusion MRI attenuated signal S(b), representative of the type of the tissue to be observed, suited to Intra Voxel Incoherent Motion (IVIM) and/or non-Gaussian signal patterns, and expressed by a model function f(b), depending on a gradient attenuation factor b and on a first set of model parameters p(i) characterizing when valued the type of tissue and the microstructure state, said model parameters p(i) defining a model parameter vector space and NP being a number of model parameters of the first set;

providing a reference model parameter vector ($p_R(i)$) corresponding to a reference state of the tissue, defining through the generic attenuation model a generic reference diffusion MRI attenuated signal $S_R(b)$; then thereafter for each model parameter p(i), determining with an image data processing device, a key b value that maximizes a partial differential sensitivity $dS_i(b)$ of the generic model diffusion MRI attenuated signal S(b) to the said model parameter p(i) at the reference model parameter vector ($p_R(i)$) over a predetermined interval of b values ranging from zero to a predetermined maximum value $b_{max}$; then thereafter determining with the image data processing device from the NP the key b values previously determined, a key b value subset by removing the key b values that are associated to model parameters of low interest for tissue type and/or the microstructure or biological state to characterize; then thereafter acquiring with the image data processing device a set of MRI images of a Field Of View (FOV) of the observed tissue by means of a motion-probing pulsed Gradient MRI sequence programmed with gradient configured to obtain the determined subset of key b values; then thereafter on a one-per-one voxel basis or on a predetermined Region Of Interest (ROI) including a set of voxels, determining with the image data processing device the signature indices that include a signature index of the voxel V or the ROI as a real number representative of the microstructure state and the type of the tissue present in the ROI or the voxel V, wherein the signature index being a scalar function depending directly on the voxel signals acquired at the key b values of the key b value subset, without using any generic attenuation model for the observed tissue;

providing a first pole parameter vector and a second pole parameter vector that correspond respectively to a calibrated high shear stiffness and a calibrated low shear stiffness, the first pole reference model parameter vector ($p_{P1}(i)$), second pole reference parameter vector ($p_{QP2}(i)$) being previously identified once for all during a preliminary calibration process carried with induced shear waves at a predetermined shear waves frequency a predetermined frequency f comprised in an interval ranging from 25 Hz to 500 Hz; then applying mechanical vibrations at the predetermined frequency f to induce shear waves in the observed tissue while acquiring a set of Magnetic Resonant Elastography images of a Field of View (FOV) of the tissue by using the two selected key b values;

then determining on a one-per-one voxel basis or on a predetermined Region Of Interest (ROI) including a set of voxels, an elasticity signature index eSnl or eSI for the predetermined frequency by using a calculation for the signature index Snl or SI, comprising further between the first step and the second step, a seventh step of:

providing a first pole reference model parameter vector ($p_{P1}(i)$) and a second pole reference parameter vector ($p_{P2}(i)$), corresponding each one to a first calibrating state P1 and a second calibrating state P2 of the same type of tissue as the observed tissue, and calculated from preliminary MRI images acquired in a preliminary step of calibration, or from previously established values, the first and second calibrating states P1, P2, as well their corresponding reference model parameter vectors ($p_{P1}(i)$),($p_{P2}(i)$), being different, wherein the signature index is a normalized signature index of a third kind, designated as Snl, that uses a signature index of a second kind Sdist and is determined by using the expression:

$$Snl(V)=\{max([Sdist(V)/Sdist1],0)-[max([Sdist(V)/Sdist2],0)]\}$$

where Sdist(V) is the second kind signature index of the voxel of the tissue under investigation, Sdist1 is the second kind signature index of the voxel of the first calibrating state P1, and Sdist2 is the second kind signature index of the voxel of the second calibrating state P2.

20. An IVIM Magnetic Resonance Elastography method for determining real IVIM elastograms and/or a contrasted shear stiffness of an observed tissue according to claim 19, wherein two sets of MRE images are acquired with phase offsets θ separated by π/2 and averaged before calculating the elasticity index eSI.

21. An apparatus for determining a signature index of an observed tissue, representative sensitively of a type of tissue or representative sensitively of a microstructure or biological state of a type of tissue, the signature indices being determined from motion-probing pulses gradient Magnetic Resonance Images (MRI) of the observed tissue, comprising:

a magnetic resonance imaging scanner to operate motion-probing pulses gradient Magnetic Resonance Imaging with a high resolution and accuracy and a means for controlling the scanner and processing the imaging data acquired by the scanner;

the magnetic resonance imaging scanner being configured for acquiring a set of MRI images of a Field Of View (FOV) of the observed biological issue by using a same motion-probing pulses gradient sequence programmed with gradient configured to obtain determined subset of key b values; and the means for controlling the scanner and processing the imaging data acquired by the scanner comprising:

a means for storing a generic attenuation model of a diffusion MRI attenuated signal S(b), representative of the type of the tissue to be observed, suited to Intra Voxel Incoherent Motion (IVIM) and/or non-Gaussian signal patterns, and expressed by a model function f(b), depending on a gradient attenuation factor b and on a first set of NP model parameters p(i) characterizing the type of tissue and the microstructure state, the said model parameters p(i) defining a model parameter vector space; and a reference model parameter vector ($p_R(i)$) corresponding to a reference state of the tissue, defining through the generic attenuation model a generic reference diffusion MRI attenuated signal $S_R(b)$; and/or a first pole reference model parameter vector ($p_{P1}(i)$) and a second pole reference parameter vector ($p_{P2}(i)$), corresponding each one to a first calibrating state P1 and a second calibrating state P2 of the same type of tissue as the observed tissue, and calculated from preliminary MRI images acquired in a preliminary step of calibration, or from previously established values, the first and second calibrating states P1, P2, as well their corresponding reference model parameter vectors ($p_{P1}(i)$), ($p_{P2}(i)$), being different a processing means configured for, for each model parameter p(i), determining a key b value that maximizes a partial differential sensitivity $dS_i(b)$ of the generic model diffusion MRI attenuated signal S(b) to the said model parameter p(i) at the reference model parameter vector ($p_R(i)$) over a predetermined interval of b values ranging from zero to a predetermined maximum value borax;

the processing means configured for determining from the NP key b values a key b value subset by removing the key b values that are associated to model parameters of low interest for tissue type and/or the microstructure or biological state to characterize;

and/or the processing means configured for calculating a neutral reference model parameter vector $p_N(i)$ as the average sum of the first pole reference model parameter vector ($p_{P1}(i)$) and the second pole reference parameter vector ($p_{P2}(i)$), when such pole reference model parameter vectors are provided; and the processing means configured for, on a one-per-one voxel basis or on a predetermined Region Of Interest (ROI) including a set of voxels, determining the signature indices that include a signature index of the voxel V as a real number representative of the microstructure state and the type of the tissue present in the ROI or the voxel V, wherein the signature index being a scalar function depending directly on the voxel signals acquired at the key b values of the key b value subset, without using any generic attenuation model for the observed tissue.

22. A non transitory computer readable storage medium having a set of non-transitory instructions configured to implement the method as defined in claim 1 when the set of non-transitory instructions are executed by a processor.

* * * * *